(12) United States Patent
Rabbani et al.

(10) Patent No.: US 9,046,537 B2
(45) Date of Patent: *Jun. 2, 2015

(54) METHOD FOR TREATING INFLAMMATION BY ADMINISTERING A COMPOUND WHICH BINDS LDL-RECEPTOR-RELATED PROTEIN (LRP) LIGAND BINDING DOMAIN

(75) Inventors: Elazar Rabbani, New York, NY (US); Xiaofeng Li, Farmington, NY (US); Dakai Liu, South Setauket, NY (US); Yazhou Zhang, South Setauket, NY (US); Richard Jin, Pennington, NJ (US); Riddhi Bhattacharyya, West Babylon, NY (US); Wei Cheng, Valley Stream, NY (US); James J. Donegan, Long Beach, NY (US)

(73) Assignee: Enzo Biochem, Inc., New York, NY (US)

( * ) Notice: Subject to any disclaimer, the term of this patent is extended or adjusted under 35 U.S.C. 154(b) by 364 days.

This patent is subject to a terminal disclaimer.

(21) Appl. No.: 12/221,863

(22) Filed: Aug. 7, 2008

(65) Prior Publication Data

US 2011/0105606 A1 May 5, 2011
US 2012/0184616 A9 Jul. 19, 2012

Related U.S. Application Data

(63) Continuation-in-part of application No. 11/598,916, filed on Nov. 14, 2006, now Pat. No. 8,367,822, which is a continuation-in-part of application No. 11/097,518, filed on Apr. 1, 2005, which is a continuation-in-part of application No. 11/084,668, filed on Mar. 18, 2005, now Pat. No. 8,461,155, which is a continuation-in-part of application No. 10/849,067, filed on May 19, 2004, now Pat. No. 8,637,506.

(60) Provisional application No. 60/504,860, filed on Sep. 22, 2003.

(51) Int. Cl.

| A01N 43/00 | (2006.01) |
|---|---|
| A61K 31/33 | (2006.01) |
| A01N 61/00 | (2006.01) |
| A61K 31/00 | (2006.01) |
| A61K 31/535 | (2006.01) |
| A01N 43/02 | (2006.01) |
| A61K 31/335 | (2006.01) |
| A01N 43/16 | (2006.01) |
| A61K 31/35 | (2006.01) |
| G01N 33/92 | (2006.01) |
| A61K 31/015 | (2006.01) |
| A61K 31/395 | (2006.01) |
| G01N 33/50 | (2006.01) |
| G01N 33/564 | (2006.01) |
| A61K 38/00 | (2006.01) |

(52) U.S. Cl.
CPC ............. *G01N 33/92* (2013.01); *A61K 31/535* (2013.01); *A61K 31/015* (2013.01); *A61K 31/395* (2013.01); *A61K 38/00* (2013.01); *G01N 33/5011* (2013.01); *G01N 33/5041* (2013.01); *G01N 33/564* (2013.01); *G01N 2333/705* (2013.01); *G01N 2800/24* (2013.01)

(58) Field of Classification Search
CPC .. A61K 31/015; A61K 31/395; A61K 31/535
See application file for complete search history.

(56) References Cited

U.S. PATENT DOCUMENTS

| 5,070,083 A | 12/1991 | Barlet et al. |
|---|---|---|
| 5,340,825 A | 8/1994 | Horwell et al. |
| 5,969,095 A | 10/1999 | Dong et al. |
| 6,204,270 B1 * | 3/2001 | Ron et al. ................. 514/263.36 |
| 6,844,422 B1 | 1/2005 | Niehrs et al. |
| 7,220,754 B2 | 5/2007 | Dijkstra et al. |
| 2003/0165500 A1 | 9/2003 | Rhee |
| 2003/0181660 A1 | 9/2003 | Todd et al. |
| 2004/0009535 A1 | 1/2004 | Brunkow |
| 2004/0023356 A1 | 2/2004 | Krumlauf |
| 2004/0038860 A1 | 2/2004 | Allen |
| 2004/0221326 A1 * | 11/2004 | Babij et al. ........................ 800/3 |
| 2004/0235728 A1 | 11/2004 | Stoch |
| 2005/0043385 A1 | 2/2005 | Guy |
| 2005/0084494 A1 | 4/2005 | Prockop |
| 2005/0196349 A1 | 9/2005 | Wu et al. |
| 2005/0244826 A1 | 11/2005 | Niehrs et al. |
| 2005/0261181 A1 | 11/2005 | Wu et al. |

(Continued)

FOREIGN PATENT DOCUMENTS

WO WO2004/084949 10/2004

OTHER PUBLICATIONS

Verma, 1997, Nature, vol. 389, pp. 239-242.*
Miyauchi, 2001, Histochem Cell Bio, vol. 116, pp. 57-62.*
Van der Vliet, H., et al. Potent expansion of human natural killer T cells using α-galactosylceramide (KPN7000)-loaded monocyte-derived dendritic cells, cultured in the presence of IL-7 and IL-15. J. Immunol. Methods 247, 61-72 (2001).
Taichman R.,et al. The Hematopoietic Microenvironment: Osteoblasts and the Hematopoietic Microenvironment. Hematol. 4(5):421-426 (2000).
Rattner A, et al. A family of secreted proteins contains homology to the cysteine-rich ligand-binding domain of frizzled receptors. PNAS. 94(7):2859-63. (1997).

(Continued)

*Primary Examiner* — Robert Landsman
(74) *Attorney, Agent, or Firm* — Anna DiGabriele Petti

(57) ABSTRACT

The present invention relates to the field of therapeutic methods, compositions and uses thereof, that affect, directly or indirectly, the behavior of LRP receptors. These compositions and methods result in the treatment of inflammatory, immunological and metabolic conditions. More particularly, the methods and compositions of the invention are directed to the identification of small molecules, drugs and/or pharmacological agents that affect the Wnt pathway by affecting normal complex formation among various signaling receptors, the LRP5 and LRP6 receptor, and related ligands.

7 Claims, 7 Drawing Sheets

(56) References Cited

U.S. PATENT DOCUMENTS

| | | | |
|---|---|---|---|
| 2006/0030523 A1 | 2/2006 | Wu et al. | |
| 2006/0127393 A1* | 6/2006 | Li et al. | 424/133.1 |
| 2006/0257892 A1 | 11/2006 | Cohen et al. | |
| 2007/0196872 A1 | 8/2007 | Bex et al. | |
| 2008/0119402 A1 | 5/2008 | Zheng et al. | |
| 2008/0318838 A1 | 12/2008 | Bauer et al. | |
| 2010/0298308 A1 | 11/2010 | Wu et al. | |

OTHER PUBLICATIONS

Yamane T., et al. Wnt Signaling Regulates Hemopoiesis through Stromal Cells. J. Immunology. 167:765-772. (2001).
Johnson et al., Journal of Bone and Mineral Research, Nov. 2004, vol. 19, No. 11:1749-1757.
Gallager, 1990, Metabolism, vol. 39, issue 4, supplement 1, Apr. 1990, pp. 27-29, abstract only.
Reya and Clevers, Nature 2005;434:843-850.
Suzuki et al., Nature Genetics 2004;36:417-422.
Itahana et al., Mol Cell. Nov. 2003;12(5):1251-1260.
Barker and Clevers, Nature Reviews: Drug Discovery 2006;5:997-1014.
Babij et al., 2003, J Bone Miner Res 18:960-74.
Bafico et al., 2001, Nat Cell Biol 3:683-6.
Bain et al., 2003, Biochem Biophys Res Commun 301:84-91.
Barrandon, Yann Mar. 20, 2003, Nature vol. 422:272-273.
Boyden et al., May 16, 2002 N Engl J Med 346(20):1513-21.
Capelluto et al. 2002, Nature 419(6908):726-9.
Cheyette et al. 2002, Dev Cell, vol. 2, 449-461.
Clark et al. 2002, J. Mol. Graph.
Culi et al. 2003, Cell 112:343-54.
Dale et al. 1998, 329:209-223.
Daniels et al 2002, 10(3):573-84.
Dann et al. 2001, Nature, vol. 412, 86-90.
Erickson et al. Mar. 1973, Journal of Lipid Research, vol. 14:133-137.
Gao, Yuan et al., May 18, 2004, PNAS, vol. 101, No. 20, pp. 7618-7623.
Glinka et al, 1998, Nature 391(6665):357-62.
Glinka et al, Jun. 10, 2002, DKFZ 2001: Research Report 1999/2000: 36-40.
Gong et al. 2001, Cell 107:513-23.
Gumbiner et al. 1998, 8:430-5 Curr Opin Genet Dev.
Guo, Nini et al. Jun. 22, 2004, vol. 101, No. 25, pp. 9277-9281.
Graham et al. 2000 Cell. 103(6):885-96.
Gruneberg, et al. 2001, Angew. Chem. Int. Ed Engl. 40, 389-393.
Hey et al. 1998. Gene 216, 103-11.
Hsieh et al. 2003, Cell 112:355-67.
Hsu et al. 1998, Molecular and Cellular Biology 18:4807-4818.
Hurst 1994 J. Chem. Inf. Comput. Sci. 34, 190-196.
Jeon et al. 2001, Nat Struct Biol 8:499-504.
Kalajzic et al. 2002, J Bone Miner Res 17(1):15-25.
Kannus et al. 2000, Osteoporos Int 11:443-8.
Kato et al. 2002, J Cell Biol 157(2):303-14.
Krupnik et al. 1999, Gene 238:301-13.
Leyns et al. 1997, Cell, vol. 88, 747-756.
Li et al. 2002, J Biol Chem 277(8):5977-81.
Li et al. 1999, EMBO J 18:4233-4240.
Li et al. 1999, J. Biol. Chem. 274:129-134.
Lips, 1997, Am J Med 103:3S-8S; discussion 8S-11S.
Little et al. 2002, Am J Hum Genet 70:11-9.
Love et al, 1995, Nature. 376(6543):791-5.
Mao et al. 2002, Nature 417:664-7.
Mao et al, 2001, Mol Cell 7:801-9.
Monaghan 1999, Mech Dev 87:45-56.
Moon RT et al, 1997, Cell, vol. 88, 725-728.
Nusse 2001, Nature 411:255-6.
Pandur et al, 2001, Bioessays 23:207-10.
Pfaffl 2001, Nucleic Acids Res May 1, 2001;29(9):e45.
Pinson et al, 2000, Nature 407:535-538.
Poy 2001, Nat Struct Biol. 8(12):1053-7.
Rarey et al, 1996 J. Mol. Biol. 261: 470-479.
Reddy, Seshamma T., et al. 2004 J Invest Dermatol 123:275-282.
Schweizer et al, 2003, BMC Cell Biol 4:4.
Semenov et al, 2001, Curr Biol 11: 951-61.
Szilagyi, Andras et al., Phys.Biol. 2 (2005) 1-16.
Takagi et al, 2003, Nature 424:969-74.
Tamai et al, 2000, Nature 407:530-5.
Tamai et al, 2004, Molecular Cell, vol. 13, 149-156.
Tolwinski et al, 2003, et al, Dev Cell 4:407-18.
Toogood, Peter. L. Apr. 11, 2002, Journal of Medicinal Chemistry vol. 45, No. 8, pp. 1543-1558.
Van Wesenbeeck et al, 2003, Am J Hum Genet 72:763-71.
von Kries et al, 2000, Nat Struct Biol. 7(9):800-7.
Waszkowycz, et al, 2001, IBM Systems J. 40, 360-376.
Wang, et al., 2005 Journal of Medicinal Chemistry, vol. 48, No. 7, 2432-2444.
Wehrli, et al, 2000, Nature 407:527-30.
Wharton 2003, Dev Biol. 253(1):1-17.
Wodarz 1998, Annu. Rev. Cell Dev. Biol. 14:59-88.
Wong et al, 2003, Mol Cell. 12(5):1251-60.
Wong et al, 2000, Nat Struct Biol. 7(12):1178-84.
Xing Y et al, 2003, Genes Dev. 2003, Nov 15;17(22):2753-64.
Wang et al., Am Chem Society, 2004.
Zuckerman 1996, N Engl J Med 334:1519-25.
Reya et al, 2005 Nature 434: 843.
Kleber et al, 2004 Curr Opin Cell Biol 16:681.
Logan et al, 2004 Annu Rev Cell Dev Biol 20: 781.
Sancho et al, 2004 Annu Rev Cell Dev Biol 20: 695-723.
Wang et al, 2004 Curr Opin Genet Dev 14: 533.
Moon et al, 2004, Nat Rev Genet 5:691.
Kawano et al, 2003, J Cell Sci 116:2627.
Zhang et al., 2004, Mol Cell Biol 24:4677-4684.
Fujino et al., 2003, Proc Natl Acad Sci USA 100: 229.
Yamazaki et al, 2003, Biochem Biophys Res Commun 304: 229.
Hoffmann et al., 1999, J Med Chem 42: 4422.
Kramer 1999, Proteins 37: 228.
Mundy et al., 1999, Science 286: 1946.
Dunstan et al., 1999, J Bone Miner Res 14:953.
Li, et al, 2001, Cell Mol Life Sci 58: 2085.
Smith, 1999, Trends Biochem Sci 24: 181.
Yuan et al, 1999, J. Biol. Chem. 274: 30419-30423.
Li et al, 2002, JBC 277; 5977-5981.
Li et al., 2005, JBC vol. 280, No. 20, 19883-19887.
Wei et al. 2006, Cell 124; 1141-1154.
Johnson et al., 2004, J Bone Disease and Mineral Research 19; 1749-1757.
Hay et al. 2005, JBC 280; 13616-13623.
Kikuchi et al., 2006, Exp Molec. Med 38; 1-10.
Semenov et al. 2005, JBC 280; 26770-26775.
Streeten et al., 2008, Bone 43(2008) 584-590.
Krane 2005, J Exp Med 201; 841-843.
Krishnan et al., 2006, J Clin Invest 116; 1202-1.
Liang et al., 2003, Cancer Cell 4:349-360.
Weeraratna et al., 2002, Cancer Cell 1:279-288.
Polakis 2000 Genes Dev 14: 1837-1851.
Behrens and Lustig 2004 Int J Dev Biol 48: 477-487.
Luu et al., 2004 Curr Cancer Drug Targets 4; 653-671.
Bafico et al., 2004 Cancer Cell 6; 497-506.
Janssens et al., 2006 Investigational New Drugs 24; 263-280.
Tian et al. 2003 NEJM 349: 2483-2494.
Oshima et al., 2005 Blood 106: 3160-3165.
Toomes et al, 2004 Am. J. Hum. Genet. 74: 751-730.
Niemann et al., 2004 Am J. Hum. Genet 74: 558-563.
Grant et al., 2006, Nature Genetics 38: 320-323.
Rodova et al., 2002 J. Biol. Chem 277: 29577-29583.
Chilosi et al., 2003, Am J. Pathol. 162: 1495-1502.
Cheon et al., 2002 Proc. Nat, Acad. Sci. (USA) 99: 6973-6978.
Miyaoka et al., 1999 Schizophr. Res. 38:1-6.
Symolon et al. 2004 J. Nutr. 134: 1157-1161.
Chen H. et al. Cell 84: 491-495, 1996.
Lee G.H. Nature 379: 632-635; 1996.
Nusse and Varmus 1982, Cell 31:99-109.
Couso et al., 1995 Development 120: 621-636.
Mukhopadhyay et al., 2001 Dev Cell 1:423-434.

(56) References Cited

OTHER PUBLICATIONS

Li et al., 2005 Nature Genetics 37:945-952.
Mukhopadhyay et al., 2006 Development 133:2149-2154.
Pinson et al., 2000 Nature 407:535-538.
Magoori et al., 2003 J Biol Chem 278:11331-11336.
Van Amerongen and Burns, 2006 Trends Genet 12:678-389.
Bockamp et al., 2002 Physiol Genomics 11:115-132.
Raport et al., 1996 J. Biol Chem 271:17161-17166.
Deng et al., 1996 Nature 382:661-666.
Dragic et al., 1996 Nature 381:667-673.
Abrami et al., 2003 J. Cell Biol 160:321-328.
Bradley et al., 2001, Nature 414:225-229.
Scobie et al., 2003 Proc Nat Acad Sci USA 100:5170-5174.
Molloy et al., 1992 J. Biol Chem 267:16396-16402.
Petosa et al., 1997 Nature 385:833-838.
Chauhan and Bhatnagar 2002, Infect Immunol 70:4477-4484.
Cunningham et al., 2002 Proc Nat Acad Sci USA 99:7049-7083.
Pannifer et al., 2001 Nature 414:229-233.
Elliot et al., 2000 Biochemistry 39:6706-6713.
Lacy et al.,2002 J. Biol Chem. 277:3006-3010.
Rosovitz et al., 2003 J. Biol Chem. 278:30936-30944.
Little et al., 1988 Infect Immun 56:1807-1813.
Lacy et al., 2004 Proc Nat Acad Sci USA 13147-13151.
Liu et al., Apr. 2007 Cell Microbiol 9(4):977-987.
Moayeri et al., 2006 Antimicrob Agents and Chemotherapy 50:2658-2665.
Schepetkin et al., 2006 J. Med. Chem. 49:5232-5244.
Goldman et al., 2006 BMC Pharmacology 6:8-15.
Panchal et al., 2004 Nat Struct Mol Biol 11:67-72.
Forino et al., 2005 Proc Natl Acad Sci USA 102:9499-9504.
Johnson et al., 2006 J. Med. Chem. 12:27-30.
Turk et al., 2004 Nat Struct Mol Biol 11:60-66.
Kocer et al., 2005 Infection and Immunity 73:7548-7557.
Karginov et al., 2005 Proc Nat Acad Sci USA 102:15075-15080.
Opal et al., 2005 Infect Immun 73:5101-5105.
Komiyama et al., 2005 Antimicrob Agents Chemotherapy 49:3875-3882.
Basha et al., 2006 Proc Nat Acad Sci USA 103:13509-13513.
E.L. Eliel & S.H. Wilen, Stereochemistry of Carbon Compounds, John Wiley & Sons, New York, NY, 1994, pp. 1119-1190.
Simon-Chazottes et al., 2006 Genomics 87:673-677.
Erlanson et al., 2004 J. Med Chem. 47:3463-3482.
Erlanson, 2006 Curr Opin Biotech 17:643-652.
Morrisey, 2003 Am J Path 162:1393-1397.
Pongracz and Stockley 2006 Respiratory Research 7:15.
Tickenbrock 2006 J Leuk Biol 79:1306-1311.
Figueroa et al., 2000 J. Histochem & Cytochem, 48(10):1357-1368.
Sen et al., 2000 Proc Nat Acad Sci USA 2791-2796.
Nakamura et al., 2005 Am J Path 167:97-105.
Gustafson and Smith 2006 J. Biol Chem 281:9507-9516.
Cawthorn et al., 2007 Cell Death Differ 14:1361-1373.
Diarra et al., 2007 Nature Medicine 13:156-163.
Rothbacher and Lemaire 2002 Nature Cell Biology 4:E172-E173.
Liu et al., 2003 Molec and Cell Biol 23:5825-5835.
Andl et al., 2002 Developmental Cell 2:643-653.
Sick et al., 2006 Science 1447-1450.
Tamamura et al., 2005 J. Biol Chem. 280:19185-19195.
Hertz and Strickland, 2001 J. Clin. Invest. 108:779-784.
Zeng et al. 2008 Development 135:367-375.
Nam et al., 2006 JBC 281(19):13247-13257.
Mercurio et al., 2003 Development 131:2137-2147.
Swiatek et al., 2006 J. Biol Chem 281:12233-12241.
Zilberberg et al., 2004 J. Biol Chem 279:17535-17542.
Guo et al., 2006 J Med Genet 43:798-803.
Mani et al., 2007 Science 315:1278-1282.
He et al., 2005 Development 131:1663-1677.
Wu et al., 2000 Curr Biol 10:1611-1614.
Zorn, 2001, Curr Biol 11:R592-R595.
Brott and Sokol, 2002 Molec and Cell Biol 22:6100-6110.
Mikels and Nusse, 2006 PloS 4:0570-0582.
Johnson et al., 2006 Genomics 88:600-609.
Pukrop et al., 2006 Proc Natl Acad Sci USA 103:5454-5459.
Lin et al., 1994 Anal Record 240:492-506.
Miyauchi et al., 2001 Histochem Cell Biol 116:57-62.
Elbashir, S. M. et al. Duplexes of 21-nucleotide RNAs mediate RNA interference in cultured mammalian cells. *Nature* 411, 494-8 (2001).
Brummelkamp, T. R., Bernards, R. & Agami, R. A system for stable expression of short interfering RNAs in mammalian cells. *Science* 296, 550-3 (2002).
Kahler, R. A. & Westendorf, J. Lymphoid enhancer factor-1 and beta-catenin inhibit Runx2-dependent transcriptional activation of the osteocalcin promoter. *J Biol Chem* vol. 278, No. 14, 11937-44 (2003).
Mundlos, S. et al. Mutations involving the transcription factor CBFA1 cause cleidocranial dysplasia. *Cell* 89, 773-9 (1997).
Otto, F. et al. Cbfa1, a candidate gene for cleidocranial dysplasia syndrome, is essential for osteoblast differentiation and bone development. *Cell* 89, 765-71 (1997).
Komori, T. et al. Targeted disruption of Cbfa1 results in a complete lack of bone formation owing to maturational arrest of osteoblasts. *Cell* 89, 755-64 (1997).
Ducy, P., Zhang, R., Geoffroy, V., Ridall, A. 1. & Karsenty, G. Osf2/Cbfa1: a transcriptional activator of osteoblast differentiation. *Cell* 89, 747-54 (1997).
Pandur, P., Lasche, M., Eisenberg, 1. M. & Kuhl, M. Wnt-11 activation of a non-canonical Wnt signaling pathway is required for cardiogenesis. *Nature* 418, 636-41 (2002).
Zhang, J, et al. Identification of the haematopoietic stem cell niche and control of the niche size. Nature 425, 836-841 (2003).
Itoh, K., Antipova, A., Ratcliffe, M. J. & Sokol, S. Interaction of dishevelled and *Xenopus* axin-related protein is required for Wnt signal transduction. *Mol Cell Biol* vol. 20, No. 6, 2228-38 (2000).
Calvi, L, et al. Osteoblastic cells regulate the haematopoietic stem cell niche. Nature 425, 841-846 (2003).
Li, Song et al., A computer screening approach to immunoglobulin superfamily atructures and interactions: Discovery of small nonpeptidic CD4 inhibitors as novel immunotherapeutics, Proc Natl Acad Sci USA vol. 94, pp. 73-78, Jan. 1997.
Willert, K, et al. Wnt proteins are lipid-modified and can act as stem cell growth factors. Nature 423, 448-452 (2003).
Gregory, C, et al. The Wnt signaling inhibitor Dickkopf-1 is required for re-entry into the cell cycle of human adult stem cells from bone marrow. The Journal of Biological Chemistry 278, (30):28067-28078 (2003).
Teitelbaum, S, et al. Genetic Regulation of osteoclast development and function. Nature Genetics 4, 638-649 (2003).
Prockop, D, et al. One strategy for cell and gene therapy: Harnessing the power of adult stem cells to repair tissues. PNAS 100, Supp. 1, 11917-11923 (2003).
Brossay, L. et al. CD1d-mediated recognition of an α-galactosylceramide by natural killer T cells is hightly conserved through mammalian evolution. J. Exp. Med. 188,(8): 1521-1528 (1998).
NIH Consensus Development Panel on Osteoporosis Prevention, Diagnosis, and Therapy, JAMA 2001, 785-795, 285.
Mao et al., LDL-receptor-related ptotein 6 is a receptor for Dickkopf proteins, Nature 2001, 321-325, 411.
Logan and Nusse, The wnt signaling pathway in development and disease, Annu, Rev. Cell Dev. Biol. 2004, 781-810, 20.
Surendran et al., A role for wnt-4 in renal fibrosis, Am J Physiol Renal Physiol 2002, F431-F441, 282.
Kelly et al., The wnt co-receptors Lrp5 and Lrp6 are essential for gastrulation in mice, Development 2004, 2803-2815, 131.
Mi and Johnson, Role of the intracellular domains of Lrp5 and Lrp6 in activating the wnt canonical pathway, Journal of Cellular Biochemistry, 2005, 328-338, 95.
Papakonstantinou et al., Matrix metalloproteinases of epithelial origin in facial sebum of patients with acne and their regulation by isotretinoin, Journal Invest Dermatol 2005, 673-684, 125.
Davidson et al., Casein kinase 1 couples wnt receptor activation to cytoplasmic signal transduction, Nature 2005, 867-872, 438.
Zeng et al., Nature 438:873-877, (2005).
U.S. Appl. No. 11/598,916, filed Nov. 14, 2006, Wu et al.

(56) References Cited

OTHER PUBLICATIONS

U.S. Appl. No. 11/097,518, filed Apr. 1, 2005, Zheng et al.
U.S. Appl. No. 10/849,643, filed May 9, 2004, Wu et al.
U.S. Appl. No. 10/849,067, filed May 19, 2004, Wu et al.
U.S. Appl. No. 11/084,668, filed Mar. 2005, Wu et al.
U.S. Appl. No. 60/965,279, Aug. 2007, Wu et al.
"C. I. Acid Blue 41-Compound Summary,"obtained on Oct. 23, 2008 from http://pubchem.ncbi.nim.nih.gov/summary/summary.cgi?cid-24200264&loc=ec_rcs.
Day et al., Dev. Cell, vol. 8 No. 5, pp. 739-750 (2005).
Delise et al , Osteoarthritis Cartilage, vol. 8 No. 5, pp. 309-334 (2000).
Dostel et al., "Acid-Base Equilibria of some 7-dimethylamino-3-phenoxazone derivative," Czechosovak Chem Commun, vol. 47, pp. 1588-1598 (1982).
Grotewold et al., Int. J. Dev, Biol., vol. 46, pp. 943-947 92002).
Kim et al., Cell, vol. 130. No. 3, pp. 470-483 (2007).
Kroot et al, "Bone mass in rheumatoid arthritis," Clinical and Experimental Rheumatology, 18 Suppl. 21. pp. S12-S-15 (2000).
Rawadi et al., "Wnt signaling pathway: a new target for the treatment of osteoporosis,"Expert Opinion Ther. Targets, vol. 9, No. 5, pp. 1063-1077 (2005).
Wei et al., The LDL Receptor-Related Protein LPR6 Mediates Internalization and Lethality of Antrax Toxin, Cell, vol. 124, pp. 1141-1154 (2006).
Westendorf et al., "Wnt signaling in osteoblasts and bone disease, "Gene, vol. 341, pp. 19-39 (2004).
Abrami et al., Anthrax toxin triggers endocytosis of its receptor via a lipid raft-mediated clathrin-dependent process, J. Cell Biol., 2003, 321-328,160.
Basha et al., Polyvalent inhibitors of anthrax toxin that target host receptors, PNAS, 2006, 13509-13513, 103(36).
Bockamp et al., Of mice and models: improved animal models for biomedical research, Physiol Genomics, 2002, 115-132, 11.
Bradley et al., Identification of the cellular receptor for anthrax toxin, Nature, 2001, 225-229, 414.
Chauhan et al., Identification of amino residues of anthrax protective antigen involved in binding with lethal factor, Infection and Immunity, 2002, 44774484, 70(8).
Couso et al., The wingless signaling pathway and the patterning of the wing margin in Drosophila, Development, 1994, 621-636, 120.
Cunningham et al., Mapping the lethal factor and edema factor binding sites on oligomeric anthrax protective antigen, PNAS, 2002, 7049-7053, 99(10).
Deng et al., Identification of major co-receptor for primary isolates of HIV-1, Nature, 1996, 661-666, 381.
Dragic et al., HIV-1 entry into CD4 cells is mediated by the chemokine receptor CC-CKR-5, Nature, 1996, 667-673, 381.
Elliot et al., A quantitative study of the interactions of bacillus anthracis edema factor and lethal factor with activated protective . . . , Biochemistry, 2000, 6706-6713, 39.
Forino et al., Efficient synthetic inhibitors of anthrax lethal factor, PNAS, 2005, 9499-9504, 102(27).
Fujino et al., Low-density lipoprotein receptor-related protein 5 (LRP5) is essential for normal cholesterol metabolism . . . PNAS, 2003, 229-234, 100(1).
Glinka et al., Dickkopf-1 is a member of a new family of secreted proteins and functions in head induction, Nature, 1998, 357-362, 391.
Goldman et al., Cationic polyamines inhibit anthrax lethal factor protease, BMC Pharmacology 2006, 1-8, 6(8).
Gong et al., LDL receptor-related protein 5 (LRP5) affects bone accrual and eye development, Cell, 2001, 513-523, 107.
Johnson et al., Defective splicing of Megl7/Lrp4, a regulator of distal limb development, in autosomal recessive mulefoot disease, Genomics, 2006, 600-609, 88.
Karginov et al., Blocking anthrax lethal toxin at the protective antigen channel by using structure-inspired drug design, PNAS, 2005, 15075-15080, 102(42).

Kato et aL., Cbfa 1-independent decrease in osteoblast proliferation, osteopenia, and persistent embryonic . . . Journal of Cell Biol, 2002, 303-314, 157(2).
Kelly et al., The Wnt co-receptors Lrp5 and Lrp6 are essential for gastrulation in mice, Development, 2004, 2803-2815, 131.
Kocer et al., Metalloproteinase inhibitors, nonantimicrobial chemically modified tetracyclines, and ilomastat . . . Infection and Immunity, 2005, 7548-7557, 73(11).
Komiyama et al., Protection from antrax toxin-mediated killing of macrophages by the combined effects . . . Antimicrobial Agents and Chemotherapy, 2005, 3875-3882, 49(9).
Lacy et al., Structure of heptameric protective antigen bound to an anthrax toxin receptor: a role for receptor in ph-dependent pore formation, PNAS, 2004, 13147-13151, 101(36).
Lacy et al., Mapping the anthrax protective antigen binding site on the lethal and edema factors, Journal of Biol. Chemistry, 2002, 3006-3010, 277(4).
Li et al., Dkk2 has a role in terminal osteoblast differentiation and mineralized matrix formation, Nature Genetics, 2005, 945-952, 37(9).
Little et al., Production and characterization of monoclonal antibodies to the protective antigen component of bacillus . . . , Infection and Immunity, 1988, 1807-1813, 56(7).
Liu et al., Characterization of the interaction between anthrax toxin and its cellular receptors, Cell Microbial, 2007, 977-987, 9(4).
Magoori et al., Severe hypercholesteroiemia, impaired fat tolerance, and advanced artherosclerosis in mice lacking . . . Journal of Biol Chemistry, 2003, 11331-11336, 278(13).
Moayeri et al,, Cisplatin inhibition of anthrax lethal toxin, Antimicrobial Agents and Chemotherapy, 2006, 2658-2665, 50(8).
Molloy et al., Human furin is a calcium-dependent serine endoprotease that recognizes the sequence arg-x-x-arg and . . . Journal of Biol. Chemistry, 1992, 16396-16402, 267(23).
Mukhopadhyay et al., Dickkopf1 is required for embryonic head induction and limb morphogenesis in the mouse, Deveopment Cell., 2001 423-434, 1.
Mukhopadhyay et al., Dkk2 plays an essential role in the corneal fate of the ocular surface epithelium, Development, 2006, 2149-2154, 133.
Nusse et al., Many tumors induced by the mouse mammary tumor virus contain a provirus integrated in the same region of the host genome, Cell, 1982, 99-109, 31.
Opal et al., Inter-alpha-inhibitor proteins are endogenous furin inhibitors and provide protection against experimental . . ., Infection and Immunity, 2005, 5101-5105, 73(8).
Panchal et al., Identification of small molecule inhibitors of anthrax lethal factor, Nature Structural & Molecular Biology, 2004, 67-72, 11(1).
Pannifer et al., Crystal structure of the anthrax lethal factor, Nature, 2001, 229-233, 414.
Petosa et al., Crystal structure of the anthrax toxin protective antigen, Nature, 1997, 833-838, 385.
Pinson et al., An LDL-receptor-related protein mediates wnt signaling in mice, Nature, 2000, 535-538, 407.
Raport et al., Molecular cloning and functional characteization for a novel human cc chemokine receptor (CCR5) for . . . Journal of Biol Chemistry, 1996, 17166-17166, 271(29).
Rosovitz et al., Alanine-scanning mutations in domain 4 of anthrax toxin protective antigen reveal residues . . . Journal of Biol Chemistry, 2003, 30936-30944, 278(33).
Schepetkin et al., Novel small-molecule inhibitors of anthrax lethal factor indentified by high-throughput screening, J. Med. Chem. 2006, 5232-5244, 49.
Scobie et al., Human capillary morphogenesis protein 2 functions as an anthrax toxin receptor, PNAS, 2003, 5170-5174, 100(9).
Turk et al., The structural basis for substrate and inhibitor selectivity of the anthrax lethal factor, Nature Structural & molecular Biology, 2004, 60-66, 11(1).
Van Amerongen et al., Knockout mouse models to study Wnt signal transduction, Trends in Genetics, 2006, 678-689, 12.
Wei et al., The LDL receptor-related protein LRP6 mediates internalization and lethality of anthrax toxin, Cell, 2006, 1141-1154, 124.

(56) References Cited

OTHER PUBLICATIONS

Ai et al., "Reduced Affinity to and Inhibition by DKK1 Form a Common Mechanism by Which High Bone Mass-Associated Missense Mutations in LRP5 Affect Canonical Wnt Signaling," *molecular and Cellular Biology*, vol. 25, No. 12, pp. 4946-4955 (2005).

Bafico et al., "Interaction of Frixxled Related Protein (FRP) with Wnt Ligands and the Frizzled Receptor Suggests Alternative Mechanisms for FRP Inhibition of Wnt Signaling, "*The Journal of Biological Chemistry*, vol. 274, No. 23, pp. 16180-16187 (1999).

Beherens et al., "Functional Interaction of B-catenin with the transcription factor LEF-1," *Nature*, vol. 382, pp. 638-642 (1996).

Berger et al., "Isolation of a candidate gene for Norrie disease by positional cloning,"*nature genetics*, vol. 1, pp. 199-203 (1992).

Berry et al., "5-Nitrofuran-2-yimethyl group as a potential bioreductivety activated pro-drug system, " *J. Chem. Soc. Perkin Trans 1*, pp. 1147-1156 (1997).

Binnerts et al., "R-Spondin 1 regulates Wnt signaling by inhibiting internalization of LRP6, "*PNAS*, vol. 104, No. 37, pp. 14700-14705 (2007).

Boucher et al., "LRP and PDGF Signaling: A Pathway to Atherosclerosis, " *TCM*, vol 14, No. 2, pp. 55-60 (2004).

Brown et al., "Isolation and Characterization of LRP6, a Novel Member of the low Density Lipoprotein Receptor Gene Family, " *biochemical and Biophysical Research Communications*, Vo. 248, pp. 879-888 (1998).

Cam et al., "Modulation of B-amyloid precursor protein trafficking and processing by the low density lipoprotein receptor family, " *Molecular Neurodegeneration*, vol. 1, No. 8, 13 pages (2006).

Caraci et al., "The Wnt Antagonist, Dickkopf-1, as a Target for the Treatment of Neurodegenerative Disorders, "*Neurochem Res*, vol. 33, pp. 2401-2406 (2008).

Carcasole et al., "Induction of Dickkopf-1, a Negative Modulator of the Wnt Pathway, IS Associated with Neuronal Degeneration in Alzheimer's Brain, " *Neurobiology of Disease*, vol. 24, No. 26, pp. 6021-6027 (2004).

Caricasole et al., "The Wnt pathway, cell-cycle activation and B-amyloid: novel therapeutic strategies in Alzheimer's disease?," *Trends In Pharmacological Sciences*, vol. 24, No. 5, pp. 233-238 (2003).

Chen et al., "Isolation and characterization of a candidate gene for Norrie disease, "*nature genetics*, vol. 1, pp. 204-206 (1992).

Chen et al., "Mechanisms of Signal Transduction: Structural Insight into the Mechanisms of Wnt Signaling Antagonism by Dkk, " *The Journal of Biological Chemistry*, vol 283, No. 34, pp. 23364-23370 (2008).

Chong et al., "Vascular Injury During Elevated Glucose Can Be Mitigated by Erythropoietin and Wnt Signaling, " *Curr Neurovasc Res.*, vol. 4, No. 3, pp. 194-204 (2007).

DasGupta et al., "Multiple roles for activated LEF/TCF transcription complexes during hair folicle development and differentiation," *Develomental*, vol 126, pp. 4557-4568 (1999).

Eastman et al., "Regulation of LEF-1/TCF transcription factors by Wnt and other signals," *Cell Biology*, vol. 11, pp. 233-240 (1999).

Eugenin et al., "HIV-tat induces formation of an LRP-PSD-95-NMDAR-nNOS complex that promotes apoptosis in neurons and astrocytes, " PNAS. vol 104, No. 9, pp. 3438-3443 (2007).

Finch et al., "Purification and molecular cloning of a secreted, Frizzled-related antagonist of Wnt action," *Proc. Natl. Acad. Sci.*, vol. 94, pp. 6770-6775 (1997).

Gaultier et al., "Regulation of tumor necrosis factor receptor-1 and the IKK-NF-kB pathway by LDL receptor-related protein explains the anti-inflammatory activity of this receptor," *Blodd*, vol. 111, No. 11, pp. 5316-5325 (2008).

Gruenberg et al., "A Functional Screen in Human Cells Identifies UBFZ as an RNA Polymerase II Transcription Factor That Enhances the b-Catenin Signaling Pathway," *Molecular and Cellular Biology*, vol. 23, No. 11, pp. 3936-3960 (2003).

Gup et al., "Polymorphisms of the low-density lipoproteinreceptor-related protein 5 (LRP5) gene are associated with obesity phenotypes in a large family-based association study," *J. Med Genet*,vol. 43, pp. 798-803 (2006).

Hammond et al., "B Strand Peptidomimetics as Potent PDZ Domain Ligands, " *Chemistry & Biology*, vol. 13, pp. 1247-1251 (2006).

Hsish et al., "A new secreted protein that binds to Wnt proteins and inhibits their activities," *Nature*, vol. 398, pp. 431-436 (1999).

Hu, "Prodrugs: Effective Solutions for Solubility, Permeability and Targeting Challenges, " *IDrugs*, vol. 7, No. 8, pp. 736-742 (2004).

Huber et al., "Nuclear localization of B-catenin by Interaction with transcription factor LEF-1," *Mechanisms of Development*, vol. 59, pp. 3-10 (1996).

Inestrosg et al., "The role of Wnt signaling in neuronal dysfuncton in Alzheimer's Disease, " *Molecular Neurodegeneration*, vol. 3, No. 9, 13 pages (2008).

Itasaki et al., "Wise, a context-dependent activator and inhibitor of Wnt signaling," *Development*, vol. 130, pp. 4295-4305 (2003).

Jaeger et al., "Functional Role of Lipoprotein Receptors in Alzheimer's Disease, "*Current Alzheimer Research*, vol. 5, pp. 15-25 (2008).

Jin et al., "The Wnt Signaling Pathway Effector TCF7L2 and Type 2 Diabetes Mellitus," *Molecular Endocrinology*, vol. 22, No. 11, pp. 2383-2292 (2008).

Johnson et al., "Diseases of Wnt signaling," *Rev Endocr Metab Disord*, vol. 7, pp. 41-49 (2008).

Jillerat-Jeanneret, Lucienne, The targeted delivery of cancer drugs across the blood-brain barrier: chemical modifications of drugs or drug-nanoparticles?, *Drug Discovery Today*, vol. 13, No. 23/24, pp. 1099-1106 (2006).

Kazanskays et al., "R-Spondin 2 is a Screted Activator of Wnt/B-Catenin Signaling and is Required of Xenopus Myogenesis," *Developmental Cell*, vol. 7, 525-534 (2004).

Kim et al., "R-Spondin Proteins: A Novel Link to etbeta;-catenin Activation," *Cell Cycle*, vol. 5, No. 1, pp. 23-26 (2006).

Kim et al., "R-Spondin Family Members Regulate the Wnt pathway by a Common Mechanism," *Molecular biology of the Cell*, vol. 19, pp. 2588-2596 (2006).

Kim et al., "New Evidence that Nuclear Import of endogenous B-Catenin is LEF-1 Dependent, While LEF-1 Independent Import of Exogenous B-Cetenin Leads to Nuclear Abnormalities," *Cell Biology International*, vol. 25, No. 11, pp. 1149-1151 (2001).

Korinek et al, "Constitutive Transcriptional Activation by a B-Catenin-Tcf Complex in APC-l-Colon Carcinoma," *Science*, vol. 275, pp. 1784-1787 (1997).

Kumar et al., "Active B-Catenin Signaling is an Inhibitory Pathway for Human Immunodeficiency Virus Replication in Perpheral Blodd Mononuclear Cells, " *Journal of Virology*, vol. 82, No. 6 pp. 2813-2820 (2008).

Lehman et al., "Duplication of Seven Exons in LDL Receptor Gene Caused by Alu-Alu Recombination in a Subject with Familial Hypercholesterolemia," *Cell*, vol. 48, pp. 827-835 (1987).

Li et al., "Sclerostin Binds to LRP5/6 and Anatagonizes Canonical Wnt Signaling[+]," *The Journal of Biological Chemistry*, vol. 286, No. 20, pp. 19883-19887 (2005).

Li et al., "LRP6 expression promotes cancer cell proliferation and tumorigenesis by altering B-cantenin subcellular distribution," *Onogene*, vol. 23, pp. 9129-9135 (2004).

Lin et al., "Wnt/B-Catenin Signaling Modulates Survival of High Glucose-Stressed Mesagial Cells," *Am Soc Nephrol*, vol. 17, pp. 2812-2820 (2006).

Liu et al., "Augmented Wnt Signaling in a Mammalian Model of Accelerated Aging," *Science*, vol. 317, pp. 803-806 (2007).

Gossen et al., "Tight control of gene expression in mammalian cells by tetracycline-responsive promoters," *Proc. Natl. Acad. Sci.*, vol. 89, pp. 5547-5651 (1992).

Gosssen et al., "Transcriptional Activation by Tetracyclines in Mammalian Cells, " *Science*, vol. 268, No. 5218, pp. 1766-1769 (1995).

Lips, Paul "Epidemiology and Predictors of Fractures Associated with Osteoporosis," *Am j Med.*, vol. 103, No. 2A, pp. 3S-11S (1997).

Liorente-Cortes et al., "LDL Receptor-Related Protein and The Vascular Wall Implications for Atherothrombosis, "*Arteriosclar Thromb Vasc Biol.*, Vol. 25, pp. 497-504 (2005).

(56) References Cited

OTHER PUBLICATIONS

Luo et al., "Wnt signaling and human diseases: what are the therapeutic implications?," *Laboratory Investigation*, vol. 87, 97-103 (2007).
Maiese et al., "Teh Wnt signaling pathway: Aging gracefully as a protectionist?," *ScienceDirect*, vol. 18 pp. 58-81 (2008).
Mani et al., "LRP6 Mutation in a Family with Early Coronary Disease and Metabolic Risk Factors," *Science*, vol. 315, pp. 1278-1282 (2007).
Manolagas et al., "Gone with the Wnts: B-Catenin, T-Cell Factor, Forkhead Box O, and Oxidative Stress in Age-Dependent Diseases of Bone, Lipid, and Glucose Metabolism," *Molecular Endocrinology*, vol. 21, No. 11, pp. 2605-2614 (2007).
Mermelstein et al., "Wnt/B-catenin pathway activation and myogenic differentiation are induce by cholesterol depletion," *Differentiation*, vol. 75, pp. 184-192 (2007).
Peters et al., "Casein Kinase I transduces Wnt signals," *Nature*, vol. 401, pp. 345-350 (1998).
Piccolo et al, "The head inducer Cerberus is a multiFunctional antagonist of Nodal, BMP and Wnt signals," *Nature*, vol. 397, pp. 707-710 (1999).
Portilno et al., "A soluble and active form of Wnt-3a protein is involved in myogenic differentiation after cholesterol depletion," *FEBS Letters*, vol. 581, pp. 5787-5795 (2007).
Rautio et al., "Prodrugs: design and clinical applications," *Nature*, vol. 7, pp. 255-270 (2008).
Rubin et al., "Secreted WNT atagonists as tumor suppressors: pro and con," *Bioscience*, vol. 11, pp. 2093-2105 (2006).
Ryu et al., "Opposing Roles of WNT-5A and WNT-11 in Interieukin-1 B Regulation of Type II Collagen Expression in Articular Chondrocytes," *J. Biol. Chem.*, vol. 281, pp. 22309-22047 (2006).
Sakanaka et al., "Casein kinase 1e in the Wnt pathway: Regulation of B-catenin function," *PNAS*, vol. 96, No. 22, pp. 12548-12552 (1999).
Schlange et al., "Autocrine WNT signaling contributes to breast cancer cell proliferation via the canonical WNT pathway and EGFR transactivation," *Breast Cancer Research*, vol. 9, 15 pages (2007).
Serrienov et al., "DKK1 Antagonizes Wnt Signaling without Promotion of LRP6 Internalization and Degradation," *J. Biol. Chem.*, vol. 283, pp. 21427-21432 (2008).
Smallwood et al., "Mutational Analysis of Norrin-Frizzled4 Recognition," *J. Biol. Chem.*, vol. 282, pp. 4057-4068 (2007).
Sprinter et al., "An Extracellular B-Proeller Module Predicted in Lipoprotein and Scavenger Receptors, Tyrosine Kinases, Epidermal Growth Factor Precursor, and Extracellular Matrix Components," *J. Mol. Biol.*, vol 283, pp. 837-862 (1998).
Streeten et al., "Quantitative Trait Loci for BMD Identified by Autosome-Wide Linkage Scan to chromosomes 7q and 21q in Men from the Amish Family Osteoporosis Study," *Journal of Bone and Mineral Research*, vol. 21, No. 9, pp. 1433-1422 (2006).
Stells et al., "Prodrug stategies to overcome poor water solubility," *ScienceDirect, Advanced Drug Delivery Reviews*, vol. 59, pp. 677-694 (2007).
Strickland et al., "Diverse roles for the LDL receptor family," *TRENDS in Endocrinology & Netabolism*, vol. 13, No. 2, pp. 66-74 (2002).
Swiatek et al., "Regulation of Casein Kinase is Activity by Wnt Signaling," *The Journal of Biological Chemistry*, vol. 279, No. 13, pp. 13011-1017 (2004).
Tamaki et al., "Insulin Facilitates the Hepatic Clearance of Plasma Amyloid B-Peptide (1-40) by Intracellular Translocation of Low-Density Lipoprotein Receptor-Related Protein 1 (LRP-1) to the Plasma Membrane in Hepatocytes," *Molecular Pharacology*, vol. 72, No. 4, pp. 850-855 (2007).
Terrand et al., "LRP1 Controls Intracellular Cholesterol Storage and Fatty Acid Synthesis through Modulation of Wnt Signaling," *J. Biol. Chem.*, vol. 284, pp. 381-388 (2009).
Uren et al., "Secreted Frizzled-related Protein-1 Binds Directly to Wingless and is a Biphasic Modulator of Wnt Signaling," *J. Biol. Chem.*, vol. 275, pp. 4374-4382 (2000).
Wan et al., "Parathyroid hormone signaling through low-density lipoprotein-related protein 6," *Genes & Development*, vol. 22, pp. 2968-2979 (2008).
Wang et al., "characterization of the Kremen-binding Site on Kkk1 and Elucidation of the Role of Kremen in Okk-mediated Wnt Antagonism," *J. Biol. Chem.*, vol. 283, 23371-23375 (2008).
Wang et al., "Frzb, a Screted Protein expressed in the Spemann Organizer, Binds and Inhibits Wnt-8," *Cell*, vol. 88, pp. 757-766 (1997).
Wehrll et al., "arrow encodes an LDL-receptor-related protein essential fro Wingless signaling," *Nature*, vol. 407, pp. 527-530 (2000).
Wei et al., "R-spondin 1 is a High Affinity Ligand for LRP6 and Induces LRP6 Phosphorylation and B-Catenin Signaling," *J. Biol. Chem.*, vol. 282, pp. 15903-15911 (2007).
Wild et al., "Global Prevalence of Diabetes," *Diabetes Caro*, vol. 27, No. 5, pp. 1047-1053 (2004).
Wright et al., "Wnt10b Inhibits Obesity in ob/ob and Agouti Mice," *Diabetes*, vol. 56, pp. 295-303 (2007).
Xu et al., "Vascular Development in the Retina and Inner Ear: control by Norrin and Frizzled-4 a High-Affinity Ligand-Receptor pair," *Cell*, vol 116, pp. 863-805 (2004).
Yang et al., "Tyrosine Phosphorylation of the LDL receptor-related protein (LRP) and activation of the ERK pathway are required for connective tissue growth factor to potentiate myofibrosiss differentiation," *The FASEB Journal*, vol. 18,vol. 18, 20 pages (2004).
Zhang et al, "Small-molecule synergist of the Wnt/B-catenin signaling pathway," *PNAS*. vol. 104, No. 18, pp. 7444-7448 (2007).
Zuthove et al., "y-Secretase Limits the Inflammatory Response Through the Processing of LRP1," *Science Signaling*, vol. 1, issue 47, 12 pages (2008).
Miyauchi et al., *Histochem Cell Bro*, vol. 116. pp. 57-62 (2001).
Verma et al., *Nature*, vol. 389, pp. 239-242 (1997).
Wei et al., "The LDL Receptor- Related Protein LPR6 Mediates Internalization and Lethality of Anthras Toxin," *Cell*, vol. 124, pp. 1141-1154 (2006).
Dostal et al., "Acid-Base Equilibria of Some 7-Dimethylamino-3-Phenoxazone Dirivatives," *Collection Czecheslavak Chem. Commun.*, vol 47, pp. 1588-1596 (1982).

\* cited by examiner

Arrangement of elements on LRP family members

A) Gallic Acid

B) Digallic Acid

Effect of Gallic Acid and Digallic Acid on Wnt activity

A) Gallic Acid

B) DiGallic Acid

Effect of Gallic Acid and Digallic Acid on Wnt activity

Effects of administration of IIC8 on tooth extraction model

A) Photographs of jaws

B) Measurements of crest distances

Effects of IIC8

A) Cytokine measurements

B) Blood glucose measurements

Alterations in Dkk-/- mouse

Alterations in Dkk-/- (KO) mouse

METHOD FOR TREATING INFLAMMATION BY ADMINISTERING A COMPOUND WHICH BINDS LDL-RECEPTOR-RELATED PROTEIN (LRP) LIGAND BINDING DOMAIN

REFERENCE TO RELATED PATENT APPLICATIONS

This application is a Continuation-in-Part of application Ser. No. 11/598,916 filed Nov. 14, 2006, now U.S. Pat. No. 8,367,822, which is a Continuation-in-Part of application Ser. No. 11/097,518 filed Apr. 1, 2005, which is a Continuation-in-Part of application Ser. No. 11/084,668 filed Mar. 18, 2005, now U.S. Pat. No. 8,461,155, which is Continuation-in-Part of application Ser. No. 10/849,067, filed May 19, 2004, now U.S. Pat. No. 8,637,506, which claims the benefit of U.S. Provisional Patent Application No. 60/504,860, filed on Sep. 22, 2003, the contents of all of which are incorporated herein by reference.

This application is related to the patent application entitled "Compositions and Methods for the Stimulation or Enhancement of Bone Formation and the Self-Renewal of Cells", by Dan Wu, et al. filed on May 19, 2004, and its entire contents is hereby incorporated by reference, in its entirety.

This application is a Continuation-in-Part of application Ser. No. 11/598,916 filed Nov. 14, 2006 now U.S. Pat. No. 8,367,822, which is a Continuation-in-Part of application Ser. No. 11/097,518 filed Apr. 1, 2005, which is a Continuation-in-Part of application Ser. No. 11/084,668 filed Mar. 18, 2005 now U.S. Pat. No. 8,461,155, which is Continuation-in-Part of application Ser. No. 10/849,067, filed May 19, 2004 now U.S. Pat. No. 8,637,506, which claims the benefit of U.S. Provisional Patent Application No. 60/504,860, filed on Sep. 22, 2003.

The contents of application Ser. Nos. 11/591,153, 11/097,518, 11/084,668, 10/849,067 and 60/504,860 are incorporated herein by reference.

BACKGROUND OF THE INVENTION

Receptors which are binding sites for proteins and small molecules are attractive targets for pharmacological intervention in disease-related processes. One group that fits this category of receptors is comprised of members of the LRP family. The term LRP is an abbreviation for LDL-Receptor-related Proteins, where the LDL receptors are a group of proteins involved in the binding and transportation of Low-density Lipoprotein (LDL) into cells by endocytosis. Various proteins are considered to be members of the LRP family because of their resemblance to LDL-receptors as well as their resemblance to each other. FIG. 1 shows various members of the LRP family, where different motifs that are held in common are shown for various members. The most important common elements are the YWTD β-propellors, EGF-like domains and LDL receptor-like ligand binding domains. These elements may appear as singular elements or they may comprise multimeric repeats. The members of this family are also characterized by a transmembrane domain that anchors the LRP extracellular portion to a membrane surface as well as an intracellular domain that may interact with cellular proteins. Although the LRP family members are structurally related, the functions they serve in vivo are of a diverse nature that include the uptake of lipoproteins, endocytosis, transcytosis, signal transduction, vitamin and hormonal homeostasis, as well as phagocytosis of necrotic cells (reviewed in Herz and Strickland 2001 J. Clin. Invest. 108:779-784). In conjunction with the various roles that these proteins may be involved in, members of the LRP family recognize a large number of ligands. For instance, one member alone, LRP1, recognizes at least 30 different ligands that in themselves represent several families of proteins. These ligands include lipoproteins, proteinases, proteinase inhibitor complexes, ECM proteins, bacterial toxins, viruses, and various intracellular proteins.

Some of the proteins that bind to members of the LRP family are involved in Wnt signaling. For example, Wnt has been shown to directly interact with one or more of the YWTD domains of the amino (extracellular) portion of LRP5 and LRP6 to induce Wnt signaling. Another example is Dkk, which is believed to bind to different domains of LRP5 and LRP6 (the third and fourth YWTD domains) but nonetheless influences the ability of the first or second domain of LRP5 and LRP6 to bind to Wnt. Other proteins such as Frat 1 (Hay et al. 2005 J Biol Chem 14; 13,616-13,623), Christin/R-spondin proteins (Nam et al., JBC 2006) and connective-tissue growth factor (CTGF) (Mercurio et al., 2003 Development 131; 2137-2147) also interact with the extracellular Domains of LRP5 while Casein kinase I (Davidson et al. 2005 Nature 438; 867-872, Swiatek et al., 2006 J Biol Chem 281; 12,233-12,241), Glycogen synthase kinase 3 (GSK3) (Mi et al., JBC 281; 4787-4794, Zeng et al., Nature 438; 873-877) and Axin (Mao et al., 2001 Mol Cell 7; 801-809) have been shown to interact with the intracellular portion. The ability to bind to a protein may or may not be involved in signal functions of an LRP molecule. For example, the majority of ligands that bind to the multiligand receptor LRP1 are either proteases or molecules associated with the control of proteolytic activity. However, although the LRP1 receptor is not commonly associated with Wnt pathway events, investigations have revealed that under appropriate conditions, truncated versions of LRP1 were able to interact with Frizzled, a major component of the Wnt signaling pathway (Zilberberg et al., 2004 J. Biol. Chem. 279; 17,535-17,542). This interaction is dissimilar to the well characterized system involving interactions of LRP5 and LRP6 and Wnt elements since the effect of both the truncated as well as the full length version of LRP1 is the opposite of the classical LRP5 and LRP6 interactions. The binding of LRP1 to Frizzled represses Wnt signaling instead of inducing it.

Some of the proteins that bind to members of the LRP family are not involved in Wnt signaling. Even with LRP members like LRP5 and LRP6, which are known to play a major part in Wnt signaling, certain ligands that bind to LRP5 and LRP6 have been shown not to affect the Wnt pathway. For instance, Wei et al. have demonstrated that LRP6 mediates the internalization and lethality of anthrax toxin (Cell 124, 1141-1154, Mar. 24, 2006), and the role of LRP5 in cholesterol metabolism is believed to be Wnt independent (Magoori et al., 2003 J. Biol. Chem. 278; 11,331-11,336). With regard to the latter, Fujino et al. (2003 Proc. Nat. Acad. Sci. (USA) 100; 229-234) investigated the metabolic consequences of a genetic ablation of LRP5 and concluded that LRP5 is essential for both normal cholesterol metabolism and glucose-induced insulin secretion. The presence of an LRP5 deficiency in either homozygous (LRP5−/−) or even heterozygous (LRP5+/−) mice resulted in a significant increase in plasma cholesterol levels when the animals were fed a high-fat diet. Although fasted blood glucose and insulin levels were normal in the mutant strains, they showed a defect in glucose tolerance when challenged. These animals also showed impaired clearance of chylomicron remnants and also impaired glucose-induced insulin secretion from the pancreatic islets. The effect of a lack of LRP5 was also tested in a double mutation situation where the mice lacked not only LRP5, but also apoE (Magoori et al. 2003). Although neither condition alone led to changes in cholesterol levels with a normal diet, the double condition led to 60% higher plasma cholesterol levels. At 6 months of age, the double-null mice had also developed severe atherosclerotic lesions that were three times larger than those in knockout mice missing only apoE. The connection between LRP molecules and metabolism is also evidenced by the discovery that certain polymorphisms in the LRP5 gene have been correlated with obesity phenotypes in a family based study (Guo et al., 2006 J. Med. Genet. 43; 798-803). Lastly, a mutation in LRP6 has been correlated to an autosomal dominant defect that results in the expression of phenotypic features associated with metabolic syndrome: hyperlipidemia, hypertension and diabetes (Mani et al., 2007 Science 315; 1278-1282.

There is a distinction between transducer (LRP5 and LRP6 receptors) and non-transducer multi-ligand receptors (non-LRP5 and non-LRP6 receptors). In the case of a non-transducing receptor, the term "multi-ligand" encompasses broad specificity, as in the case of a receptor that takes up different monosaccharides. In this case, essentially the same effect (transport) is carried out by the receptor for a variety of different ligands where each internalized ligand is then recognized and processed according to its specific chemical nature. On the other hand, for multi-ligand signal receptors, another layer of complexity is observed where different domains participate in different reactions. In the case of signal transducers, the ligand per se is not the target of further downstream actions. In fact, as a rule, it is not even internalized. Thus, the specificity of the signal transduction is entirely the result of the specificity of the transducer. This means that if two different ligands elicit two different downstream responses, there must be a difference, however subtle, in the way they trigger the transducer after binding.

With regard to the LRP5 and LRP6 receptor, it is quite obvious that the extracellular and intracellular domains must by necessity have different ligands and different functions. Even within the extracellular portion itself, there will be differentiation of function for the different domains of LRP5 and LRP6. For example, the first two YWTD domains in the extracellular portion of LRP5 and LRP6 are involved in binding Wnt and transmitting a signal, while the third and fourth domains are sites for binding of a completely different protein, Dkk, and a subsequent dampening of Wnt signaling. Remarkably, LRPs combine features of both types of multi-ligand receptors since they can function both as an internalizer and as a transducer.

Although domains of functional and structural similarity can be identified through amino acid alignments, the ability of such analogues to carry out different functions is a product of their fine differences. As described in the review article by Herz and Stickland that was cited earlier: "Crystallographic and nuclear magnetic resonance studies of individual repeats have revealed that the sequence variability in short loop regions of each repeat results in a unique surface contour surface and charge density for each repeat." In summary, even when a collection of repeated sequences are able to form similar structures, the particular nature of the amino acids on their exposed surfaces will still dictate the ability to bind different ligands. Interactions between individual amino acids will also cause differences in the overall structure where cavities in comparable domains may be slightly larger or smaller due to small scale attractive or repulsive forces. This can be seen in the studies of LRP5 and LRP6 where the size of the opening in the β-propeller of a YWTD repeat region is different from one domain to another. More importantly, as described in section 4.2 of U.S. Patent Application No. 20050196349, identification of amino acid residues that are important for Dkk binding was carried out by alanine scanning. A comparison of nucleic acid and amino acid sequences shows that there are substitutions of different amino acids at analogous sites (U.S. patent application Ser. No. 11/598,916) within these cavities thereby differentiating the degree of affinity between molecules that may be similar in size but different in terms of polarity and/or charge with regard to binding to each of the domains.

In the previously cited patent applications, the use of a detailed three-dimensional model of the LRP5 receptor allowed a virtual screening of a library of compounds for predicting molecules that would fit into a binding domain of LRP5. As disclosed in U.S. Patent Application No. 20050196349, a variety of different biological results can be seen when these compounds are tested with in vitro assays. Looking at Table II, it can be seen that some of the compounds (Group 1) are toxic as exemplified by compounds IIC5, IIIC6, and IIIC12 which reduced basal expression to 26%, 0% and 10%, respectively. Not surprisingly, further experiments showed a lack of stimulation when Wnt was added. Other compounds such as IIC6, IIC18 and IIC19 were not intrinsically toxic, since they maintained or even stimulated basal level expression. However, in this group of compounds (Group 2), the addition of Wnt showed no stimulation, indicating an inability to respond to Wnt in the presence of these compounds. A third class of compounds (Group 3) showed a normal level of response to the addition of Wnt compared to the no drug control, but showed a diminished effect of inhibition by Dkk. For instance, IIC8 (NCI 39914) allowed essentially the same level of stimulation by Wnt as in its absence (1227 compared to 1000 in the absence of drug), but when Dkk was added, the amount of activity was only reduced to 476. The control showed a shift of 1000 to 100 by the addition of Dkk. Even more strikingly, IIIC3 (NCI 8642) shows almost the same amount of activity in the presence of Dkk as in its absence, demonstrating that the binding of this molecule can lead to a block in Wnt suppression by Dkk. There is even one compound, IIC9, that represents a fourth group of compounds that was able to reduce the amount of Wnt stimulation, but instead of showing Dkk suppression, Wnt activity was stimulated three fold by the presence of Dkk. Thus, it can be seen that binding to LRP5 and LRP6 does not necessarily lead to a single phenotype in these assays.

There are a variety of reasons why these different effects may be seen. For instance, although one particular domain was chosen for the selection of a ligand from the library, a biological assay may reveal that the affinity of the compound is higher for a different (but similar) domain on the target protein. There is also the possibility of mimicry, where the binding of the compound to the Dkk site on LRP5 and LRP6 in itself emulates the same effect seen by binding of the true ligand and leads to "Dkk-like" suppression of Wnt activity in the absence of Dkk. It is also natural to assume, especially in the case of a multi-ligand receptor, that allosteric effects are possible that influence separate binding events at sites away from where the drug itself may bind.

In the previously disclosed applications, molecules with properties described for the third class of compounds (Group 3) were tested for various biological activities besides the LEF reporter system in order to test for a biological effectiveness for disease processes. Among the assays described in these disclosures were those related to bone formation and remodeling as witnessed by assays for osteoblast differentiation in U.S. Patent Application No. 20050196349. Two compounds from this group, IIC8 and IIIC3, were tested for an additional property, the ability to block the binding of sclerostin, a protein which has previously been shown to have an effect similar to that of Dkk in being able to block Wnt signaling. Experimental results showed a direct correlation where increased amounts of these compounds resulted in decreased binding of sclerostin-AP. These compounds as well as other similar compounds were also tested for effects on bone growth via calavarial bone formation, β-catenin activity and viability in various tumor cell lines, tumor induction in a mouse model, as well as metabolic effects such as cholesterol and glucose metabolism (U.S. patent application Ser. No. 11/598,916). The potential use of pharmaceutical compositions for altering the activity of LRP5 in a subject has been described in U.S. Patent Application No. 20030181660 (hereby incorporated by reference) with specific application to diseases such as diabetes, autoimmune diseases, viral infections, osteoporosis and metabolic disorders, as well as diseases that involve or affect endocytosis, antigen presentation, cytokine clearance or inflammation. However, their approach was directed towards a different level, where they taught the use of compounds to regulate the level of expression of LRP5. In contrast, the methods described in U.S. Patent Application No. 20050196349 have been directed towards the identification of compounds that interact with the LRP5 and LRP6 protein or associated proteins.

A similar program of virtual screening followed by binding studies was carried out for compounds predicted to bind to Disheveled, another member of the Wnt signaling pathway (U.S. patent application Ser. No. 11/097,518). In this case, molecules of interest were followed with testing for effects on embryogenesis.

SUMMARY OF THE INVENTION

The present invention discloses the identification and use of molecules that bind to members of the LRP family thereby providing for relief in subjects suffering from inflammation, an immune mediated disorder, a metabolic disorder, a pathological condition associated with an elevation of TNF-α, a pathological condition associated with elevation of mmp, a skin condition or disease, an organ or tissue injury or any combination of the foregoing. Other molecules that may be of use in the present invention may bind to a factor that interacts with an LRP thereby preventing its binding to LRP, where the disruption of this binding may also provide relief from the foregoing conditions.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

Figure 1:
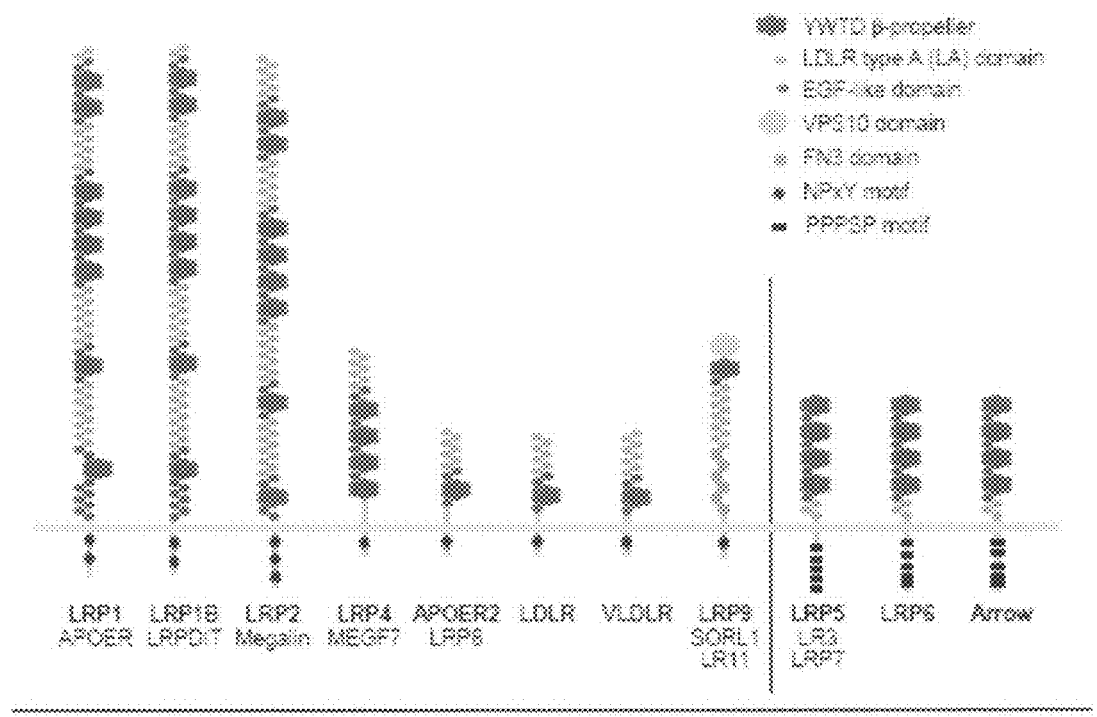
FIG. 1 is a diagram of the structure of various members of the LRP family showing the location of various motifs (taken from FIG. 2 of He et al. "LDL Receptor-Related Proteins 5 and 6 in Wnt/b-catenin Signaling: Arrows Point the Way" 2005 Development 131; 1663-1677).

In the previously cited U.S. Patent Application No. 20050196349, a methodology was disclosed that was successful in identifying pharmacological agents that can influence Wnt activity in a subject. Various procedures, including mutational analysis, alanine scanning, crystallography, NMR spectroscopy, homology modeling, and three dimensional models of target proteins involved in the Wnt pathway, were all used for virtual screening of a library of compounds to select compounds capable of binding to selected portions of targets involved in protein-protein interactions.

By binding to these elements, the present invention discloses that beneficial effects may be induced either by influencing Wnt signaling or by taking advantage of non-Wnt signaling effects that are also properties of the LRP signal receptors. In many cases, differentiation between these signaling routes is not necessary, since only the net effect may be of interest rather than the particular mechanism. Thus, when carrying out screening assays, the particular effect may be ascertained for a molecule based upon effects on a marker for the Wnt pathway, or a biological assay may be carried out that does not directly monitor Wnt signaling and serves as a marker for only the desired result. As an example of the latter, the ability to alter the amount of TNF-α in a subject can be an effect-oriented assay that measures the amount of TNF-α secreted by cells in the presence of a molecule that is being tested for pharmaceutical efficacy. In a similar fashion, any of a variety of animal models that are used for induction of inflammatory responses may be used for testing of effects by molecules that have been selected on the basis of being able to bind to LRP or to one of the elements that interact with LRP.

In U.S. Patent Application No. 20050196349 ("the '349 Application"), virtual screening allowed the selection of a number of molecules that were subsequently tested for their ability to bind to LRP5 and LRP6. Success in this approach was seen by the high number of molecules from this screen that were able to affect the binding of a alkaline-phosphatase labeled Dkk molecules to full length LRP5 (see Table I of the '349 Application). A variety of effects were seen where some compounds induced an inhibitory effect of the binding of the labeled Dkk to LRP and other compounds were actually able to induce an increased level of binding. In a further step, the molecules were tested with a biological assay for an ability to inhibit a Wnt-mediated assay. Therefore, in Tables II and III of the '349 Application, molecules selected for an affinity for the Dkk binding site of Domain III of LRP5 had various effects on Wnt activity, where some showed no effects, some increased Wnt activity and some showed decreased Wnt activity. In a second biological assay, Wnt activity was also measured in the presence of Dkk, a repressor of Wnt activity. In this particular application, only molecules that lacked effects upon Wnt activity but were able to alleviate Dkk suppression of Wnt activity were used as model molecules for a further screening step. However, although this particular biological assay was applied, that the ability of a molecule to bind to LRP6 may provide therapeutical benefits should not be ruled out because of an inability to negate Dkk-mediated Wnt suppression.

The complexity of the Wnt system can also be seen in FIG. 21 of U.S. patent application Ser. No. 11/598,916 where a dose dependency curve showed differential effects: at low dosages, the binding of ENZO M01 Dkk blocked repression of Wnt signaling and it declined as the dosage was increased. However, at higher concentrations there is a reversal of this effect and with increasing dosages there was an actual increase in Wnt activity. As previously disclosed in U.S. patent application Ser. No. 11/598,916, because of the similarity of the domains in LRP5 and LRP6, the selection of an agent for binding to one domain may also be a selection of an agent that has affinity for an unselected, but similar domain. This would be especially true for another domain on the LRP5 and LRP6 receptor but as mentioned earlier, analogous YWTD Domains are present on other members of the LRP family as well. With reference to multi-targeting of LRP5 Domains, modeling experiments with the predicted structure of a LRP6 in conjunction with the structures of IC15 and IIIC3 show that although IIIC3 shows excellent fitting within the cavity of the YWTD Domain III used for the virtual screening described in the '349 Application, another molecule, IC15, selected on the same basis actually shows a better fit with YWTD Domain II, indicating that it may have a higher affinity for this domain rather than the one used in the screening. A similar effect may be taking place in some examples, where at low concentrations, YWTD Domain III is occupied by a selected compound, but at a higher concentration, the lower affinity targets Domain I or II may be occupied, and thereby either decrease the amount of Wnt that can bind or otherwise hinder its ability to transmit a signal. Although the inventors have not carried out investigations of compounds that in the absence of Dkk either: a) knocked down Wnt activity; or b) acted as a stimulator of Wnt activity, these compounds may have higher affinities for Domains I and/or II rather than the Domain III structure used in the virtual screening. In the former case, the compounds may reduce Wnt activity by decreasing the amount of Wnt that can bind or interfere with Wnt signal transmission and in the latter case, the compounds may mimic the binding of Wnt and provide their own stimulatory signal.

As a result of the multiplicity of similar Domains on even a single LRP receptor as well as the similarity between the various LRPs, a molecule selected to bind to the Dkk binding Domain of LRP6 may have a variety of physiological effects that may or may not be associated with Dkk binding and furthermore, these effects may or may not be associated with the Wnt pathway. With regard to the latter case, the selection of a molecule for binding to the Dkk binding site may be viewed as using a site for binding in general. Given that these receptors are signal generating moieties that depend upon binding events and likely allosteric rearrangements, a binding of a molecule to one particular site may have profound effects on the binding at other sites as well as the activity of the receptor for other functions that are carried out at other sites. The present invention takes advantage of the fact that an LRP receptor with a bound ligand will have altered properties compared to a receptor without a ligand. As such, the present invention discloses that either one of two approaches may be appropriate after identification of a binding molecule. In the first approach, a mechanistic methodology is employed where a particular stepwise pathway is used in assays, where the ability of being able to relieve Dkk suppression is used as a criterion for use in Wnt activation (or more explicitly blockage of Dkk suppression of Wnt), as identified by a surrogate marker such as the LEF reporter gene. This was the approach taken in the previously cited applications and it has been shown to result in the identification of a number of useful compounds. Applicants now disclose that a more functional approach may also be taken that eschews mechanisms and looks at applications instead. In this approach, the ability to bind to the LRP receptor is the basis of selection, but then direct effects upon the physiological problem are assessed rather than the LEF surrogate marker.

This direct approach may result in the identification of more compounds than might not be apparent with only the mechanistic approach. For instance, it is known that Dkk1 and Dkk2 have mutually antagonistic effects such that under some circumstances Dkk1 represses Wnt activity but Dkk2 leads to induction or enhancement (Wu et al., 2000 Curr Biol 10; 1611-1614; Zorn 2001 Curr Biol 11; R592-R595; Brott and Sokol 2002 Molec and Cell Biol 22; 6100-6110). Thus, when a molecule is selected for prevention of binding of other proteins to LRP5 and LRP6 by virtue of the structure of the Dkk binding site of LRP5 and LRP6, both Dkk1 and Dkk2 interactions are potentially affected. As such, a pharmacological agent that binds to this site may have entirely opposite effects depending upon whether the activity is based upon a cellular environment where binding of Dkk1 or Dkk2 is more important. As such, evaluation of a net clinical effect may be of more importance than that of individual steps. This will especially hold true in animal studies where numerous different cell types are involved in both disease manifestation as well as possible curative processes. The importance of cellular milieu for Wnt signaling has been noted before for Dkk2 where it can act as a Wnt repressor or activator and in a paper by Mikels and Nusse (2006 PloS 4; 0570-0582) where Wnt5a can either activate or inhibit a β-catenin reporter gene. Lastly, it was earlier disclosed that LRP1 can affect Wnt signaling and that LRP4, another member of the LRP family has been considered to be involved in the Wnt signaling system due to its similarity to LRP5 and LRP6 in the organization and sequences of its extracellular domains and the effects on limb development by mutations in the gene coding for LRP4 (Johnson et al. 2006 Genomics 88; 600-609, Simon-Chazottes et al., 2006 Genomics 87; 673-677). As such, selection of a compound that binds to a β-propellor region of LRP5 or LRP6 may also be a selection for an agent that binds to other members of the LRP family as well with results that may affect roles that these other LRP members participate in that may be different form those of LRP5 and LRP6.

It has been previously described in U.S. patent application Ser. No. 11/598,916 that either component of a protein/protein interaction may be a candidate for pharmaceutical intervention with identified compounds (as described in U.S. patent application Ser. Nos. 10/849,643, 10/849,067, 11/084, 668, 11/097,518, 11/598,916, 60/963,771 and 60/965,279). These compounds may include a small molecule, protein, peptide, polypeptide, cyclic molecule, heterocyclic organic molecule, nucleic acid, lipid, charged lipid, polar lipid, non-polar lipid, sugar, glycoprotein, glycolipid, lipoprotein, chemical, or a fragment of a compound that comprises a heterocyclic organic molecule, nucleic acid, lipid, charged lipid, polar lipid, non-polar lipid, sugar, glycoprotein, glycolipid, lipoprotein, or chemical. Thus, it is also a subject of the present invention that ligands that bind to LRP molecules may also be targets, where the same methods previously described for identifying compounds that bind to LRP receptors may also be applied to the ligands that bind directly and indirectly to LRP receptors.

Another object of the present invention is to subdivide core compounds that have been found to affect the selected targets into subcores that may also bind to the selected targets. These subcores may also be used to identify additional effective compounds. For example, IIIC3 (illustrated below) was used to identify the following core compound 1a:

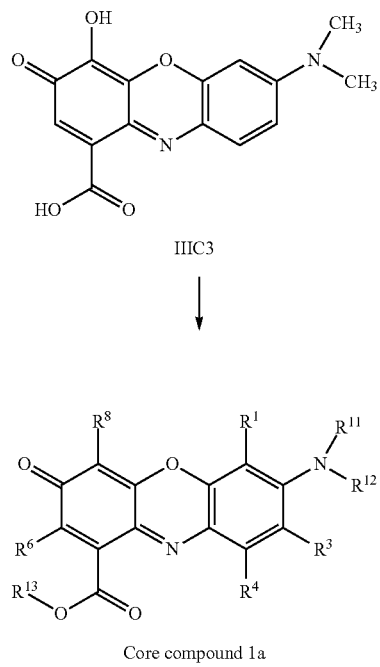

IIIC3

Division of IIIC3 results in the two following components:

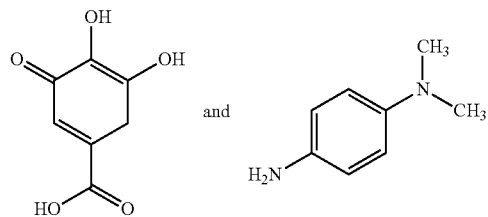

which can be described as separate subcores with the following structures:

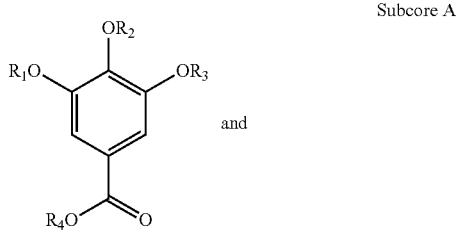

Subcore A

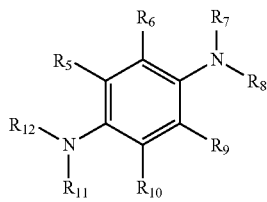

Subcore B

Figure 2:
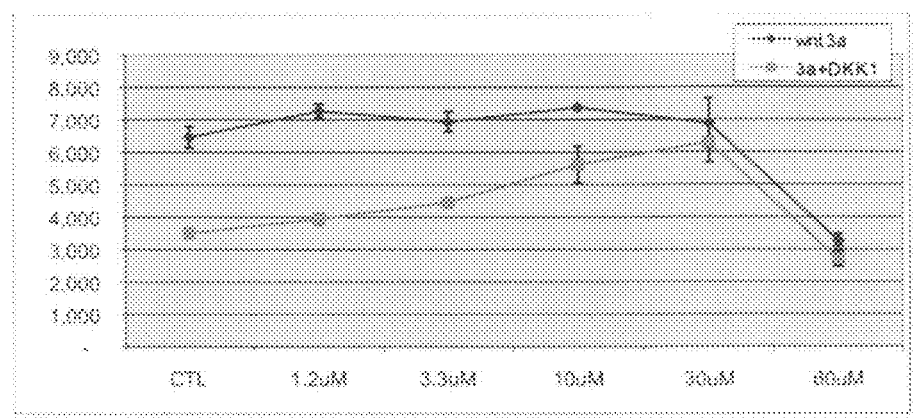
FIG. 2A-B is graphs showing the effects of various concentrations of Gallic Acid (Panel A) and Digallic Acid (Panel B) upon Wnt activity and the suppression of Wnt activity by Dkk.
Figure 2:
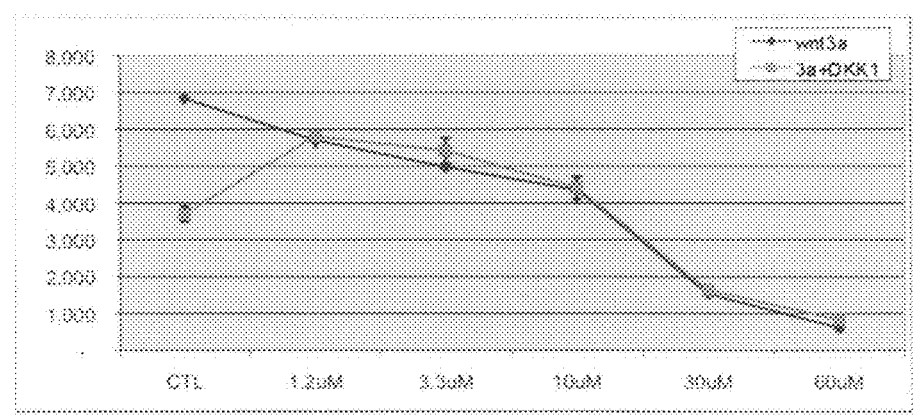

This reductionist approach may be exploited by virtual screening where the subcore is added to various other groups and tested for a predicted ability to bind to the target structure. Alternatively, some empirical experiments may also be carried out where molecules that correspond to these subcore regions are obtained or synthesized and tested out in appropriate bioassays. In some cases there may be similar effects to the parent core compound by the subcore compound whereas in other cases the subcore requires additional contacts provided by other parts of the parent core molecule to provide sufficient binding ability to the target protein to provide a biological effect. As an illustration of this approach, Gallic Acid, which is a small molecule similar to the Subcore A shown above, was tested for its effect upon Wnt activity. The results are described in Example 1 and shown in FIG. 2 where it can be seen that the a small molecule derived form the subcore of Core compound 1a (Gallic Acid) can by itself block the effects of Dkk repression.

If a subcore is sufficiently small and has been shown to have some degree of effectiveness, it may be used to design a dimeric molecule. This dimeric molecule will be especially useful when the target region comprises repeated amino acid sequences such that the region that provides a binding site for the subcore is present in multiple copies i.e., a first subcore of the dimer can bind to one portion of the target while a second subcore of the dimer binds to its corresponding region in the same binding area. For instance, a dimeric compound can be made and tested with either Subcore A or Subcore B shown above. An illustration of this point is described in Example 2 and FIG. 3 where a dimeric version of Gallic Acid was tested and shown to be effective at a concentration where Gallic Acid itself has no effect, indicating an enhanced affinity for the multimeric form compared to the monomeric form. If the target regions are large enough, more than two subcores can be joined together to bind to various repeat units of the target region.

In contrast, if the binding subdomains of the target are dissimilar, it may be more useful to append a different chemical group to the first subcore to provide additional binding ability. This particular circumstance will arise when the target region is not made up of repeat units. It may also arise when repeated units are used for structural comformation but the amino acids that are exposed as contact points are the sites where the repeat sequences diverge from each other. To use the exemplary IIIC3 molecule above, the binding affinity of the core compound to LRP may be considered to be a summation of the binding abilities of Subcore A (essentially a Gallic Acid moiety) to bind to one site and the ability of Subcore B to bind to another site within the target region. In the absence of thermodynamic data concerning the particular contribution from each moiety, it is unknown whether there are similar levels of binding stabilization endowed by each moiety or whether it may be disproportionate in nature. It is even possible that the observed binding from a molecule is sufficiently asymmetric that most of the affinity of the compound derives from one subcore and the major contribution of the other subcore is only a neutral aspect, i.e. not interfering with the ability of the first subcore to bind. In this type of case, there would be opportunity for obtaining a more effective compound, by partnering the functional subcore with a different compound that can more actively contribute to binding.

There are a variety of ways that a subcore may be partnered with other chemical moieties to identify a more effective pharmaceutical agent. Reviews of such methods are summarized in Erlanson et al., 2004 (J Med Chem 47; 3463-3482) and Erlanson 2006 (Curr Opin Biotech 17; 643-652) for a process termed fragment based drug discovery. This can take the form of virtual screening where various groups are appended to the subcore and predictions on binding capability are carried out followed by biological assays similar to the way compounds were first identified. Alternatively, it may occur by the empirical testing of compounds that comprise the subcore, linked to other chemical groups. With either approach, the compounds that are selected to be added to the subcore may be those that have been identified as subcore moieties derived from other compounds that have exhibited desirable properties, or they may be of an uncharacterized or unselected nature.

As mentioned above, the aforementioned complex effects may be explained by the possibility that pharmacological agents are binding to more than one domain that is present in multiple copies in the target protein. Advantage of this can be taken on a broader scale than that described in the present invention regarding subcore moieties by linking pharmacological agents together that are too large to fit into a single domain together. They may comprise a homodimer (or more) of identical or similar compounds, or they may comprise different agents. Although proteins such as LRP5 and LRP6 are frequently drawn as linear molecules with domains, akin to knots on a string, there may be flexing and bending of these proteins such that protein domains may be in closer physical proximity than depicted in relevant diagrams. As such, a multimeric pharmacological agent that is formed by linking together two or more previously selected pharmacological agents may allow for situations where the binding of one agent to a high affinity domain will enhance the binding of a tethered second version of the agent to a lower affinity domain, thereby creating new properties that would not be enjoyed by a monomeric agent at that concentration. Furthermore, since there may be compounds that optimally bind to different domains (see discussion of IC15 and IIIC3 above) utility may also be found in creating a multimeric compound that comprises two different molecules with their own specific affinities to potentially: a) increase the overall affinity for the complex to the target; b) provide a wider range of targets that may be bound by the compound; and c) exhibit synergistic effects. There may also be bifunctional binding to more than one protein by a single multimeric pharmacological agent since dimerization and multimerization of proteins is a common biological phenomenon that would provide proximity between domains from different proteins.

The connection between Wnt signaling and inflammation is a complex issue where Wnt may be part of a number of disease processes such as pulmomary fibrosis (Morrisey 2003 Am J Path 162; 1393-97; Pongracz and Stockley 2006 Respiratory Research 7; 15), leukocyte inflammatory responses (Tickenbrock 2006 J Leuk Biol 79; 1306-1311) and diabetes (Figueroa et al. 2000). Increased levels of Wnt have also been seen in diseases such as rheumatoid arthritis where it has been associated with increased levels of markers for inflammation such as IL-6, IL-8 and IL-15 in one study (Sen et al., 2000 Proc. Nat. Acad. Sci. (USA) 2791-2796) and TNF-α, IL-1β and IL6 in another (Nakamura et al., 2005 Am J Path 167; 97-105). In Nakamura et al., a direct connection between Wnt and the latter set of inflammatory markers was shown by transfecting cells with Wnt 7b and observing a significant increase in the level of all three of the markers. The opposite experimental analysis was carried out by Gustafson and Smith (2006 J Biol Chem 281; 9507-9516) where treatment of adipocytes with additional exogenous TNF-α increased Wnt expression and IL6 resulted in an increase of the apparent phosphorylation of frizzled, both events leading to a block in differentiation of the adipose cells. The effects of the Wnt pathway on adipogeneseis can also be seen where treatment with TNF-α resulted in the stabilization of β-catenin. (Cawthorn et al., 2007 Cell Death Differ 14; 1361-1373). This latter effect could be reversed in a β-catenin knockout mouse where the blockage of adipogenesis by TNF-α was noticeably attenuated.

Rheumatoid arthritis is a disease that is marked by the presence of both increased Wnt and inflammatory cytokines. This is not surprising since the manifestations of this autoimmune disease involve bone reabsorption as well as inflammation processes. A transgenic mouse has been developed as a model for rheumatoid arthritis in humans by transformation with human TNF, thereby replicating many of the features of the disease. When this animal model was administered a Dkk-1 antibody, the result was the prevention of bone loss (Diarra et al. 2007 Nature Medicine 13; 156-163). However, it was also found that there was an "uncoupling" where there was also no significant change in histopathological indications showing that a beneficial effect was only conveyed for part of the syndrome. Presumably, the anti-Dkk blocked repression by native Dkk molecules and allowed increased Wnt expression to thereby ameliorate the bone loss problem. Since increased Wnt levels are associated with inflammation, it is not surprising that the inflammatory process continued in this study despite the treatment. In contrast, it was discovered that the use of a small molecule selected for its ability to bind to the domain on LRP6 which is involved in Dkk binding gave a surprising and unanticipated event. In the animal model system used in Example 4, the pharmacological agent was able to duplicate the ability of anti-Dkk to prevent bone loss but in contrast to the antibody results, the administration of the small molecule also led to a reduction in the inflammation marker, TNF-α (see Example 4).

In addition, Li et al. described the use of anti-Dkk as a treatment for inflammatory processes in U.S. Patent Application No. 20060127393. This application was mainly concerned with improvements in the nature of the anti-Dkk antibodies and there were no working examples provided for demonstrating a reduction in inflammation by means of their antibody. Furthermore, in light of the work cited above by Diarra et al., there is no evidence that the anti-Dkk antibody is capable of providing relief of inflammation.

It is a further teaching of the present invention that agents that bind to LRP molecules, or to associated ligands or molecules, may have indirect effects. For example, the binding of Kremen to Dkk and LRP5 and LRP6 is believed to lead to endocytosis of a ternary complex (reviewed in Rothbacher and Lemaire 2002 Nature Cell Biology 4; E172-E173) thereby decreasing the effective amount of LRP5 and LRP6 on the surfaces of cells. As such, the inhibition of binding between Dkk and LRP5 and LRP6 should result in a higher level of LRP5 and LRP6 remaining on the surface of the cells. Conversely, pharmacological agents that increase binding between LRP5 and LRP6 and Dkk should lead to increased sequestration of LRP5 and LRP6 and a net decrease in its presence. These actions may influence the effects of any proteins that interact with LRP5 and LRP6, Dkk or Kremen and as discussed previously, these proteins may or may not be involved in Wnt signaling. The effects of such an increase may also be complex in nature. For instance, it has been found that depending upon context, the effects of overexpression may be different between LRP5 and LRP6. An overabundance of LRP5 has been reported to lead to increased levels of β-catenin (Kato et al., J Cell Biol 157; 303-314) and an overabundance of LRP6 has been described to lead to increased Wnt signaling (Liu et al., 2003 Molec and Cell Biol 23; 5825-5835). However, Mi and Johnson (J Cell Biochem 95; 328-338) observed a difference between LRP5 and LRP6, where heightened levels of LRP6 led to increased signals from the TCF/LEF marker, whereas LRP5 had no effect. Although the baseline level of signaling was different, both the LRP5 transfected cells as well as the LRP6 cells still showed evidence of increased signaling when Wnt was added.

Furthermore, different components of the Wnt system have different feedback loops that affect each other's level of transcription. For example, the use of siRNA to knock down the amount of Dkk provides a transient increase in Wnt activity, but this is counterbalanced by the presence of motifs in the promoter for Dkk leading to upregulation of transcription from the Dkk. The amount of Dkk activity may be equal to the initial amount or it may be higher or lower, depending upon the amount of transcription carried out. This may provide at least a partial explanation for the results of the anti-Dkk antibody discussed above.

Pharmacological agents found capable of binding to LRP or to an LRP associated protein may find use with other processes that have been found associated with the Wnt pathway. For example, it has been recently discovered that Wnt activity has been linked to hair follicle formation (Aandl et al., 2002 Developmental Cell 2; 643-653; Sick et al., 2006 Science 1447-1450) and as such some of the compounds of the present invention may be used to ameliorate hair loss problems. In addition, a group of proteins called matrix metalloproteinases (mmps) have been found to be associated with skin biology during inflammatory matrix remodeling neovascularization, wound healing and malignant transformation as well as less serious conditions such as acne (Papakonstantinou et al., J Invest Dermatol 125; 673-684). Some of these mmps, including MMP2, MMP3, MMP7 and MMP9, have been described as targets of the Wnt signaling pathway (Tamamura et al., 2005 J Biol Chem 280; 19,185-19,195). The mmps may also illustrate a connection between Wnt activity and inflammation since treatment of breast cancer cells with Wnt5a led to induction of MMP7 which is known to release TNF-α (Pukrop et al., 2006 Proc. Nat. Acad. Sci (USA) 103; 5454-5459). Therefore, certain compounds of the present invention may possess curative processes for disease conditions associated with mmps.

The terms "immune modulation" should be understood to mean the modification of one or more components of the immune system to either enhance or inhibit the activity or amount of that component or components. Modulation may also include a simultaneous enhancement of one or more components accompanied by inhibition of one or more other components.

The terms "immune disorders" are diseases involving the immune system that can include but not be limited to allergies, autoimmune diseases, immune complex diseases, immunodeficiency diseases and cancers of the immune system.

The term "autoimmune diseases" may include but not be limited to Acute disseminated encephalomyelitis, Addison's disease, Ankylosing spondylitisis, Antiphospholipid antibody syndrome, Aplastic anemia, Autoimmune hepatitis, Autoimmune Oophoritis, Coeliac disease, Crohn's disease, Diabetes mellitus, Gestational pemphigoid, Goodpasture's syndrome, Grave's disease, Guillan-Barre syndrome, Hashimoto's disease, Idiopathic thrombocytopenic purpura, Lupus erythematosus, Multiple sclerosis, Myasthenia gravis, Opsoclonus myoclonus syndrome, Optic neuritis, Ord's thyroiditis, Pemphigus, Pernicious anemia, Polyarthritis, Primary biliary cirrhosis, Rheumatoid arthritis, Reiter's syndrome, Sjogren's syndrome, Takayasu's arteritis, Warm autoimmune hemolytic anemia, and Wegener's granulomatosis.

The term "chronic inflammatory diseases" may include but not be limited to Tuberculosis, Chronic cholecystitis, Bronchiectasis, ulcerative colitis, silicosis and other pneumoconiosis as well as the above listed autoimmune diseases The term "small molecule" is means a non-peptide molecule of 10,000 or less molecular weight.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "therapeutically effective amount" means the amount of the subject compound that will elicit the biological or medical response of a tissue, system, animal or human that is being sought by the researcher, veterinarian, medical doctor or other clinician. As used herein, the term "treatment" refers to both to the treatment and to the prevention or prophylactic therapy of the mentioned conditions, particularly in a patient who is predisposed to such disease or disorder.

The term "treating" in its various grammatical forms in relation to the present invention refers to preventing, (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

The term "LRP ligand" is a protein involved in a protein-protein interaction with at least one member of the LRP receptor family. Ligands include proteins, lipoproteins, proteinases, proteinase inhibitor complexes, ECM proteins, bacterial toxins, viruses and various intracellular and extracellular proteins. Examples of ligands that are known to interact with LRP5 and LRP6 include Wnt, Sclerostin (SOST), Wise, DKK and Frizzled (Frz).

EXAMPLES

Examples provided are intended to assist in a further understanding of the invention. Particular materials employed, species and conditions are intended to be further illustrative of the invention and not limited of the reasonable scope thereof.

Example 1

Effects of Gallic Acid and Digallic Acid on Wnt and Dkk Suppression of Wnt

This experiment was carried out as previously described in U.S. Patent Application No. 20050196349 using Gallic Acid, a small molecule that represents a partial constituent of the IIIC3 molecule as well as Digallic Acid, which represents a dimeric form of Gallic Acid. The structures of Gallic Acid and Digallic Acid are provided below:

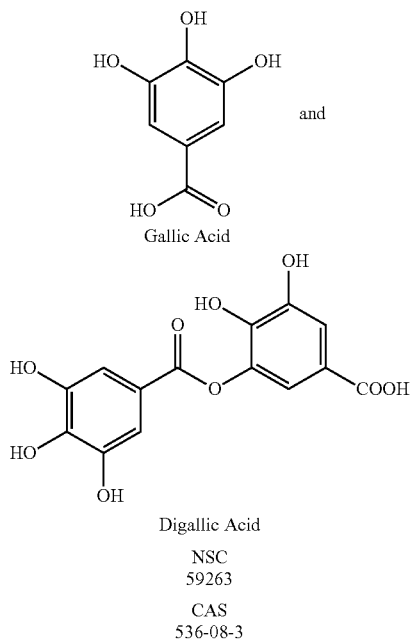

Gallic Acid

Digallic Acid
NSC 59263
CAS 536-08-3

As seen in FIG. 2A, the small molecule derivative of IIIC3 is capable of providing protection against Dkk suppression when present at 30 mM. In this experiment, the Digallic Acid completely blocked Dkk at even the lowest (1.2 mM) value tested.

Example 2

Effects of Digallic Acid on Wnt and Dkk Suppression of Wnt

Figure 3:
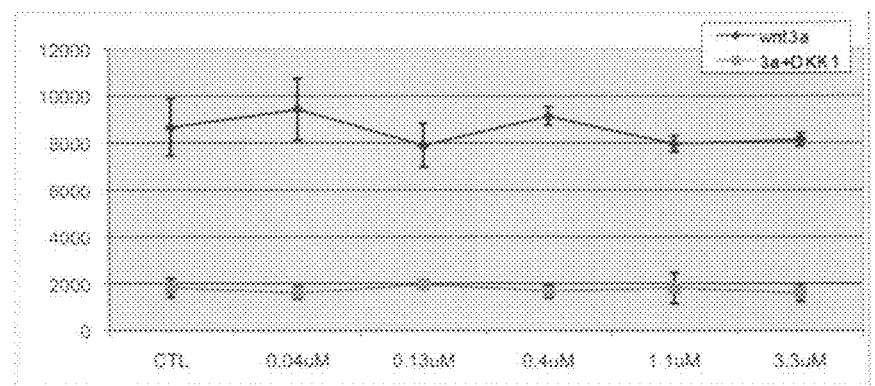
FIG. 3A-B is graphs showing the effects of lower concentrations of Gallic Acid (Panel A) and Digallic Acid (Panel B) upon Wnt activity and the suppression of Wnt activity by Dkk.
Figure 3:
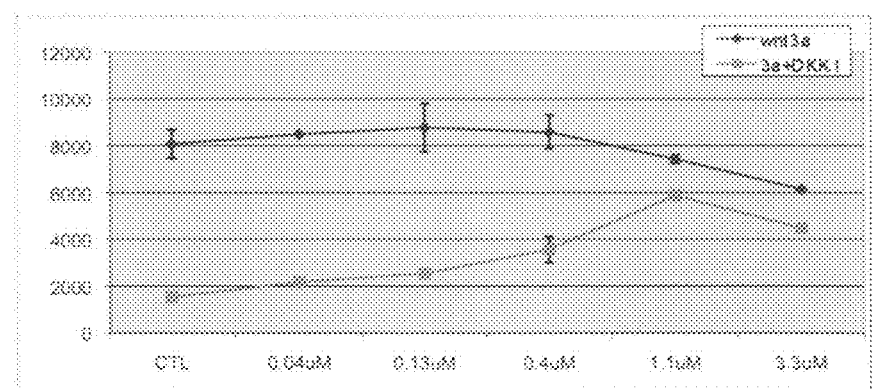

This experiment was carried out as described above except that a lower range of drug dosage was used as compared to Example 1. In FIG. 3A, there is essentially no effect upon either Wnt activity or suppression of Wnt activity by Dkk when up to 3.3 mM Gallic Acid was present (similar to what was seen with Example 1, FIG. 2A). In contrast, FIG. 3B shows that modest effects upon Wnt activity at the higher (1.1 and 3.3 uM) dosages and a dose dependent effect upon inhibition of Dkk suppression showing that the dimeric form is much more potent than the monomeric form. Both FIGS. 2 and 3 indicate that nearly 30 times as much Gallic Acid had to be present to achieve the same effect as the dimeric Gallic Acid.

Example 3

Stimulatory Effects of Enzo IIC8 on Alveolar New Bone Formation in a Tooth Extraction Model A root extraction model (Lin et al., 1994 Anat Record 240; 492-506) was used to determine whether IIC8 (described in U.S. Patent Application No. 20050196349) is able to stimulate new bone formation. The bone regeneration process following tooth extraction is a complex phenomenon that involves wound healing, as well as bone formation. Briefly, the initial coagulum is followed by the formation of woven bone, lamellar bone, bone marrow, and cortical bone. At the cellular level this process involves induction and regulation of growth of several distinct cell types, as well as differentiation of stem cells into several cell types. The point of the experiment described below was to determine whether a drug could accelerate the process of bone growth without adversely affecting the end product of the process.

Procedure: 10 week old Sprague Dawley rats (~300 gram body weight obtained from Taconic Farms, Germantown, Pa.) were anesthetized. They then underwent extraction of left and right first maxillary molars followed by filling of the empty tooth sockets with gel foam. The animals were than treated both topically and systemically with the test compound. In Group A, 8 rats were injected with 10 μl of 5 mg/ml IIC8 dissolved in PBS. In Control Group B, 8 rats were injected with 10 μl of PBS. At approximately 12 hr intervals the animals were injected with additional 10 ml aliquots of IIC8 (Group A), or PBS (Group B). At the same time, the animals were also injected IP with 1 ml of IIC8 (Group A), or with 1 ml of PBS (Group B). This treatment was carried out in five day cycles, followed by two days of rest, for a total duration of 3 weeks. At 7 days intervals, two animals from each group were sacrificed and their maxillae were excised, fixed, and decalcified. After dehydration, the specimens were sectioned along the molars in a mesio-distal plane followed by staining with hematoxylin and eosin.

Figure 4:
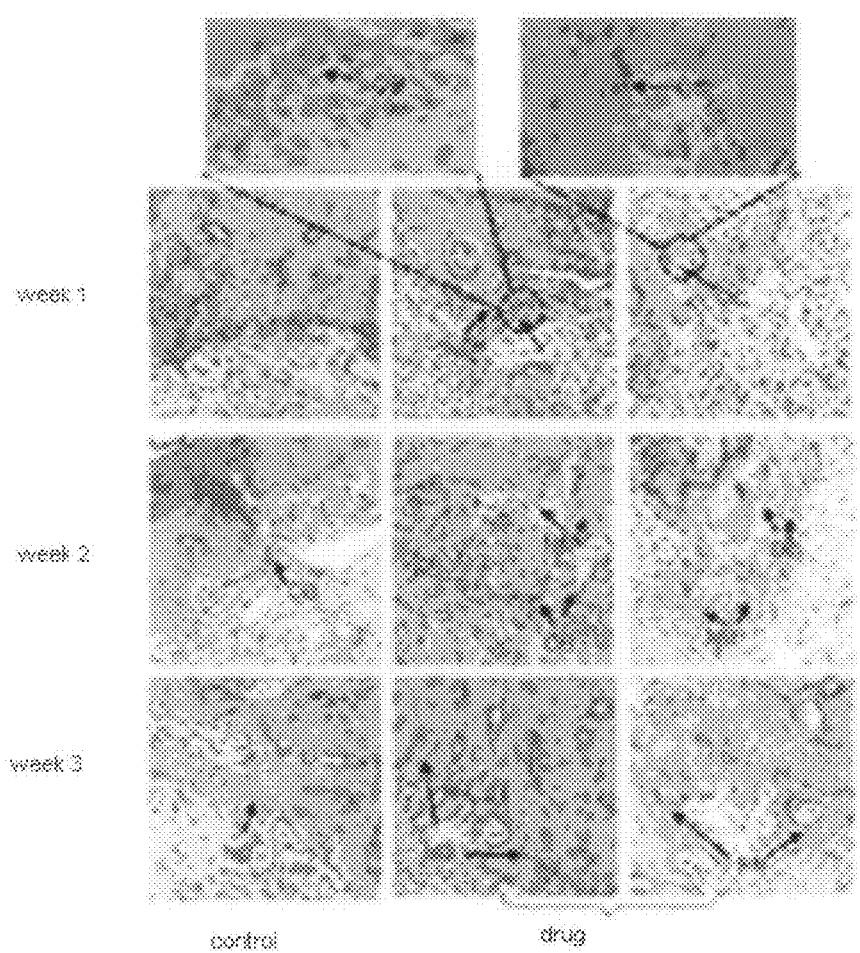
FIG. 4 is a picture of the effects of IIC8 on new bone formation.

Results: As shown in FIG. 4A, after one week of treatment, the IIC8 treated animals already exhibit a large number of osteoblast cells, indicating significant osteoblast differentiation/proliferation and osteoblastic activity. Osteoclast cells are also seen, indicating that bone remodeling and reconstruction is in process with a notable amount of new bone being deposited. In contrast, very few osteoblast or osteoclast cells are found in the control group (FIG. 4).

After 2 weeks of treatment, an overwhelming number of osteoblast cells were found inside the extracted tooth sockets of the IIC8 treated animals, with a decreased number of osteoclast cells relative to the samples from week one, indicating an extremely high level of anabolic activity. There was a significant amount of mineralized new bone formed at this stage.

Animals in the PBS control group also had osteoblast cells after two weeks, which confirms that the remodeling process is triggered by the tooth extraction and thus is active, though to a lesser extent, even in the absence of any drug treatment.

After 3 weeks of treatment, the specimens showed reduced osteoblastic activities in both IIC8 and PBS groups. However, in the IIC8 treated group, there was a significant amount of mineralized new bone throughout the socket. In contrast, new bone formation was seen only in a few small areas of the control group.

Conclusion: The tooth extraction model, a standard model of bone formation and remodeling, shows that IIC8 significantly stimulates both processes relative to the untreated controls. Thus IIC8 can be utilized as an agent that promotes osteogenesis and upregulates anabolic activity. Additionally, the concomitant topical and systemic administration proved free of undesired (toxic) effects, which provides considerable leeway in the design of a therapeutic regimen.

Example 4

Potency of Enzo IIC8 in the Prevention of LPS-Induced Periodontal Bone Loss

IIC8 was tested in an animal model of periodontitis (Miyauchi et al. 2001 Histochem Cell Biol. 116:57-62) that was used to evaluate cytokine production in rat molar gingival periodontal tissues after topical application of lipopolysaccharide (LPS). LPS is a complex glycolipid that represents a major component of the outer membrane of Gram-negative bacteria, which are well established etiological agents of periodontitis.

Remarkably, with regard to periodontitis, LPS alone can mimic the effect of a bacterial infection, by establishing an inflammatory condition that eventually leads to periodontal tissue destruction. Thus, the model is well suited to test for drugs that help prevent bone loss elicited by massive inflammation.

Procedure: Sprague Dawley rats (~300 gram body weight obtained from Taconic Farms, Germantown Pa.) were treated with LPS, or with PBS, by injection into the maxillary labial and palatal gingival between first and second upper molars on both sides. The injections were repeated two more times on an every other day basis, for a total of three treatments.

Three groups were investigated:
Group A: PBS-treated, 10 animals
Group B: LPS-treated, 10 animals
Group C: LPS- and IIC8-treated, 12 animals For Group C, 1 ml of 5 mg/ml IIC8 was administered per os daily starting from three days prior to the initial LPS injection for a total duration of 10 days.

At the conclusion of treatments, animals were euthanized and their maxillary jaws excised and defleshed. The defleshed jaws were then soaked in 0.2N NaOH for 5 min at room temperature to remove the remaining soft tissue and analyzed under a dissection microscope.

Figure 5:
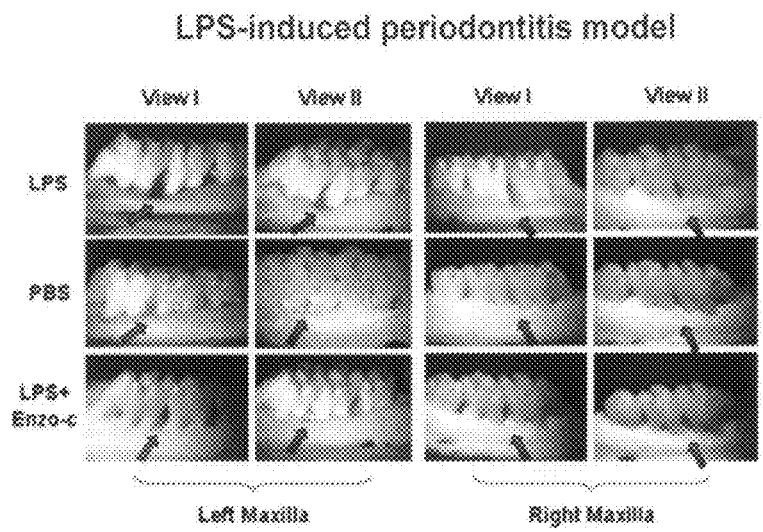
FIG. 5A-B is pictures (Panel A) and a graph (Panel B) relating to bone loss in periodontitis and the effectiveness of compound IIC8 in its treatment. Panel A is pictures showing protection against bone loss in LPS-induced periodontitis with macroscopic images of jaws. Arrows indicate the sites between the first and second molars where LPS or control saline was injected. View I is a front view and View II is a top view. Panel B is a graph showing measurements of average distances between Cemento-enamel junctions (CEJ) and alveolar crests, indicating the degree of bone loss in a periodontal model.
Figure 5:
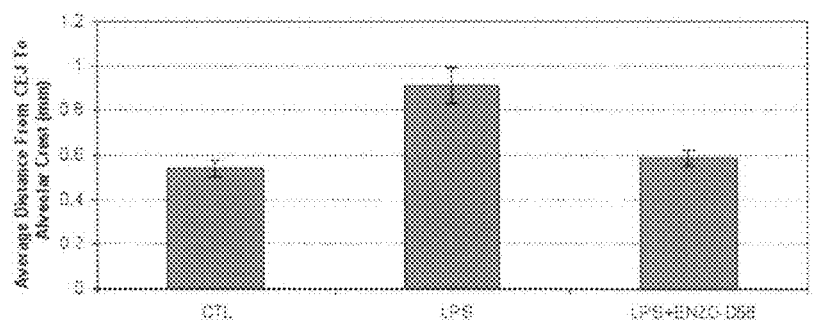

Results: Inspections of the jaws under dissection microscope showed that animals treated with IIC8 had significantly more alveolar bone than those in the LPS-only control group. FIG. 5A is a macroscopic image of the palatal sides of the maxillary jaws. The control with the LPS administration showed severe bone resorption with root furcation exposure, demonstrating the major destructive impact LPS has in this animal model system. On the other hand, there is very limited loss of the alveolar bone in the group of animals that have been administered compound IIC8 as well as the LPS, showing a highly protective effect by this compound. Although it can be seen by the naked eye that the IIC8 conferred beneficial effects in this system, a duplicate experiment was carried out and measurements were made between the cementoenamel junctions (CEJ) and the alveolar crests to obtain numerical data. A second experiment was also carried out and quantitative measurements were taken. The defleshed jaws were stained with Leoffler's methylene blue in order to identify the cemento-enamel junction (CEJ) as a reference point to measure bone height. Histological analysis clearly showed significant bone resorption and root furcation in the LPS-treated animals, and little bone resorption in the LPS plus SMTC-treated animals. Linear measurements from the CEJs to the alveolar bone crest showed a mean bone loss of 0.94±0.08 mm in LPS-treated animals; 0.59±0.04 mm in LPS plus SMTC-treated animals; and 0.54±0.04 in control animals. There were statistically significant differences between the LPS group and the LPS plus SMTC group (p=0.00006) and between the control group and LPS group (p=0.00003). As an indicator of protection, there was no significant difference between the control group and the LPS plus SMTC group (p=0.18). These data clearly show that SMTC protects against bone resorption in an animal model of endotoxin-induced bone loss. This SMTC may represent an attractive potential new class of therapeutic agents for clinical use.

Quantitative results were also obtained by measurements of TNF-α, which as described previously is a major marker for inflammatory processes. The results of this assay were as follows:

| Group A: PBS-treated | 59.7 |
| Group B: LPS-treated | 102.9 |
| Group C: LPS- and IIC8-treated | 65.2 |

It should be pointed out that although the differences between Group A and B as well as between Group B and C were highly significant (P values of 0.0001 for each), the difference between Groups A and C was not considered to have significance (tailed P value equals 0.3479), i.e. the untreated controls and the subjects treated with IIIC8 in addition to the LPS are statistically undistinguishable. This shows that in addition to either preventing bone loss or compensating for its loss, the IIIC8 compound was also able to reduce inflammation that had been the primary cause of the disease process of the animal model. It also serves as an example that the compounds of the present invention may have utility in wound healing processes.

Example 5

Characterization of DKK(−/−) Mice

The complexity of the interplay between LRP5 and LRP6, Dkk and inflammation was examined by testing the effects of inflammatory responses in knockout mice that had Dkk2 eliminated (this mutation was previously described in U.S. Patent Application No. 20050261181). Also tested were heterozygous Dkk (Dkk2+/0) mice where due to gene dosage effects there should be lower intrinsic levels of Dkk present.

Figure 6:
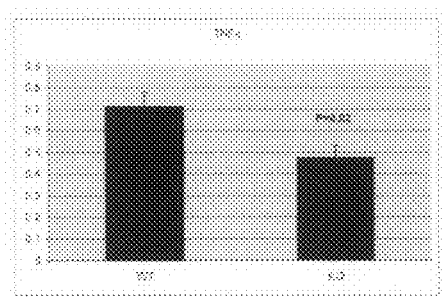
FIG. 6A-B is graphs showing the effects of Dkk mutations on TNFα parameters (Panel A) and blood glucose levels (Panel B).
Figure 6:
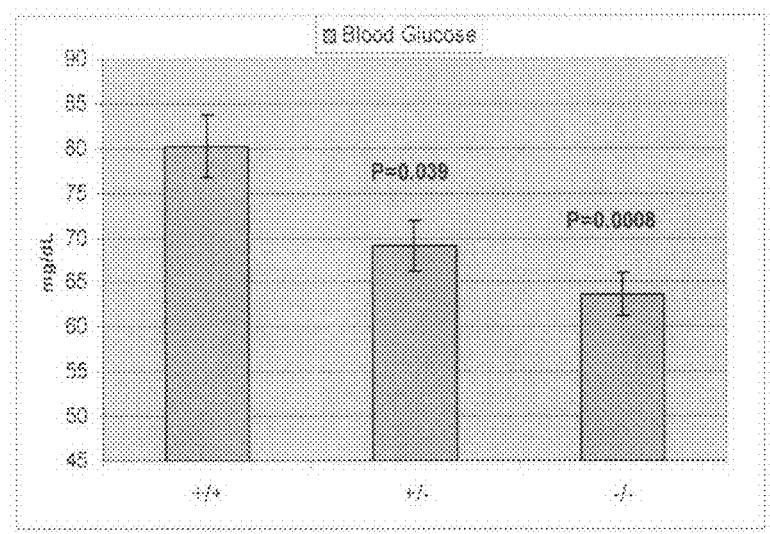
Figure 7:
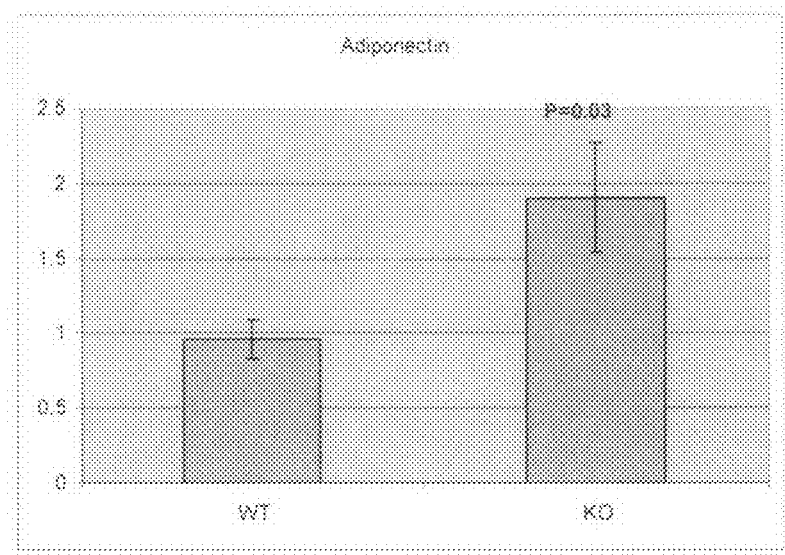
FIG. 7 is a graph showing the effects of Dkk(−/−) mutation on Adiponectin levels.

Results: Various parameters are shown in FIG. 6 and FIG. 7 where major differences may be seen for TNF-α levels (FIG. 6A), blood glucose levels (FIG. 6B) and Adiponectin (FIG. 7).

The invention claimed is:

1. A method for treating inflammation in a subject, comprising the administration of a therapeutically effective amount of a compound to said subject, wherein said compound binds to an LDL-receptor-related protein (LRP) ligand binding domain, wherein the LRP is LRP-5 or LRP-6 and the ligand is selected from Dickkopf protein (Dkk) or sclerostm, and wherein said compound is a cyclic molecule or a heterocyclic organic molecule.

2. The method of claim 1, wherein said inflammation is caused by an autoimmune disease or a chronic inflammatory disease.

3. The method of claim 2, Wherein said inflammation is caused by Acute disseminated encephalomyelitis, Addison's disease, Ankylosing spondylitis, Antiphospholipid antibody syndrome, Aplastic anemia, Autoimmune hepatitis, Autoimmune Oophoritis, Coeliac disease, Crohn's disease, Diabetes mellitus, Gestational pemphigoid, Goodpasture's syndrome, Grave's disease, Guilian-Barre syndrome, Hashimoto's disease, Idiopathic thrombocytopenic purpura, Lupus erythematosus, Multiple sclerosis, Myasthenia gravis, Opsoclonus myoclonus syndrome, Optic neuritis, Ord's thyroiditis, Pemphigus, Pernicious anemia, Polyarthritis, Primary biliary cirrhosis, Rheumatoid arthritis, Reiter's syndrome, Sjogren's syndrome, Takayasu's arteritis, Warm autoimmune hemolytic anemia, or Wegener's granulomatosis.

4. The method of claim 2, wherein said inflammation is caused by Tuberculosis, Chronic cholecystitis, Bronehiectasis, ulcerative colitis, silicosis or another pneumoconiosis disease.

5. The method of claim 1, wherein said inflammation is caused by Crohn's disease or periodontitis.

6. The method of claim 1, wherein said compound is:

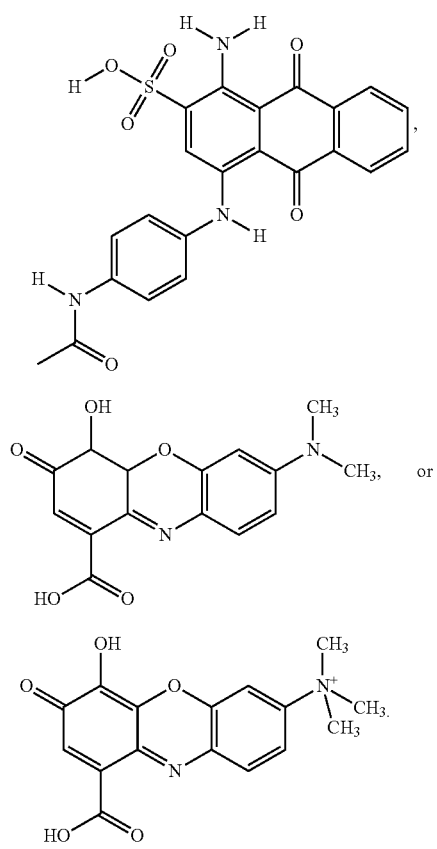

7. A method of treating inflammation caused by Crohn's disease in a subject comprising administration of a therapeutically effective amount of a compound to the subject selected from

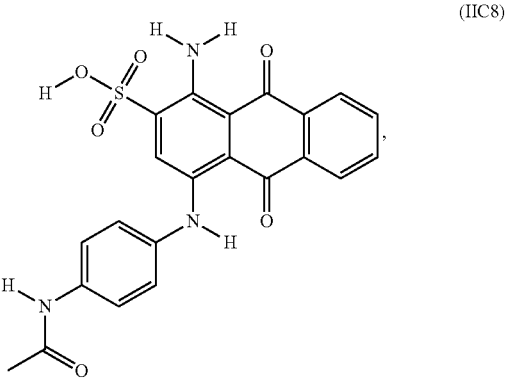

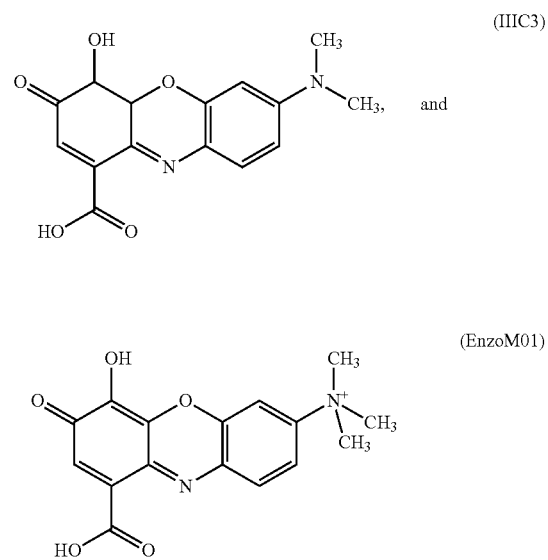

wherein said compound binds to an LDL-receptor-related protein (LRP) ligand binding domain, wherein the LRP is LRP-5 or LRP-6 and the ligand is selected from Dkk or sclerostin.

* * * * *

UNITED STATES PATENT AND TRADEMARK OFFICE
CERTIFICATE OF CORRECTION

| | | |
|---|---|---|
| PATENT NO. | : 9,046,537 B2 | Page 1 of 1 |
| APPLICATION NO. | : 12/221863 | |
| DATED | : June 2, 2015 | |
| INVENTOR(S) | : Rabbani et al. | |

It is certified that error appears in the above-identified patent and that said Letters Patent is hereby corrected as shown below:

In the Claims

In claim 1, at col. 18, line 56, "sclerostm" should read "sclerostin."

In claim 3, at col. 18, line 62, "Wherein" should read "wherein."

Signed and Sealed this
Seventeenth Day of May, 2016

Michelle K. Lee
*Director of the United States Patent and Trademark Office*